(12) United States Patent
Peng et al.

(10) Patent No.: US 6,653,529 B2
(45) Date of Patent: Nov. 25, 2003

(54) USE OF THE MAIZE X112 MUTANT AHAS 2 GENE AND IMIDAZOLINONE HERBICIDES FOR SELECTION OF TRANSGENIC MONOCOTS, MAIZE, RICE AND WHEAT PLANTS RESISTANT TO THE IMIDAZOLINONE HERBICIDES

(75) Inventors: Jianying Peng, Durham, NC (US); Lynne Hirayama, Mercerville, NJ (US); Christian Lochetto, Yardley, PA (US)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 09/845,917

(22) Filed: Apr. 30, 2001

(65) Prior Publication Data

US 2003/0167538 A1 Sep. 4, 2003

Related U.S. Application Data

(60) Provisional application No. 60/200,658, filed on Apr. 28, 2000.

(51) Int. Cl.$^7$ .................. C12N 15/29; C12N 15/82; A01H 4/00; A01H 5/00
(52) U.S. Cl. ............... 800/278; 435/418; 435/419; 435/468; 800/300; 800/300.1; 800/320.2; 800/320.3
(58) Field of Search .................. 435/6, 468, 413, 435/418, 419; 800/278, 300, 300.1, 320.1, 320.2, 320.3, 298

(56) References Cited

U.S. PATENT DOCUMENTS

| | | | |
|---|---|---|---|
| 4,761,373 A | 8/1988 | Anderson | 800/300.1 |
| 5,013,659 A | 5/1991 | Bedbrook et al. | 536/23.2 |
| 5,141,870 A | 8/1992 | Bedbrook et al. | 435/320.1 |
| 5,545,822 A | 8/1996 | Croughan | 800/300 |
| 5,591,616 A | 1/1997 | Hiei | 435/469 |
| 5,731,180 A * | 3/1998 | Dietrich | 800/278 |
| 5,750,866 A | 5/1998 | Dietrich et al. | 800/278 |
| 5,767,361 A * | 6/1998 | Dietrich | 800/300 |
| 5,853,973 A | 12/1998 | Kakefuda et al. | 435/4 |
| 5,928,937 A | 7/1999 | Kakefuda et al. | 435/320.1 |
| 5,981,840 A * | 11/1999 | Zhao et al. | 800/294 |
| 6,025,541 A * | 2/2000 | Dietrich et al. | 800/278 |
| 6,153,812 A * | 11/2000 | Fry et al. | 800/288 |

FOREIGN PATENT DOCUMENTS

| | | | |
|---|---|---|---|
| WO | WO 92/08794 | * | 5/1992 |
| WO | WO 99/11757 A1 | | 3/1999 |

OTHER PUBLICATIONS

Li et al. 1992, A sulfonylurea herbicide resistant gene from *Arabidopsis thaliana* as a new selectable marker for production of fertile transgenic rice plants. Plant Physiology 100:662–668.*

Hansen et al 1999, Trends in Plant Science 4(6):226–231.*
Bowen 1993, Transgenic Plants vol. 1, pp. 89–123, Academic Press, Inc., San Diego; S. Kung and R. Wu eds.*
Anderson PA, Georgeson M (1989) Herbicide–tolerant mutants of corn. Genome 31: 994–999.
Aldemita RR, Hodges TK (1996) *Agrobacterium tumefaciens*–mediated transformation of japonica and indica rice varieties. Planta 199: 612–617.
Barett M (1989) Protection of grass crops from sulfonylurea and imidazolinone toxicity. pp 197–220.
Brown MA, Chiu TY, Miller P (1987) Hydrolytic activation versus oxidative degradation of Assert herbicide, an imidazolinone aryl–carboxylate, in susceptible wild oat versus tolerant corn and wheat. Pestic Biochm Physiol 27: 24–29.
Chaleff RS, Mauvais CJ (1984) Acetolactate synthase is the site of action of two sulfonylurea herbicides in higher plants. Science 224: 1443–1445.
Chaleff RS, Ray TB (1984) Herbicide–resistant mutants from tobacco cell cultures. Science 223: 1148–1151.
Chan MT, Lee TM, Chang HH (1992) Transformation of Indica rice (*Oryza sativa* L.) by *Agrobacterium tumerfaciens*. Plant cell Physiol 33: 577–583.
Charest PJ, Hattori J, DeMoor J, Iyer VN, Miki BL (1990) In vitro study of transgenic tobacco expressing Arabidopsis wild type and mutant acetohydroxyacid synthase genes. Plant cell Rpt 8: 643–646.
Christou P, Ford TL, Kofron M (1991) Production of transgenic rice (*Oryza sativa*) from agronomically important Indica and Japonica varieties via electric discharge particle acceleration of exogenous DNA into immature zygotic embryos. Bio/Tech 9:957–962.
Haughn GW, Smith J, Mazur B, Somerville C (1988) Transformation with a mutant Arabidopsis acetolactate synthase gene renders tobacco resistant to sulfonylurea herbicide. Mol Gen Genet 211: 266–271.
Hayashimoto Z, Li A, Murai N (1990) A polyethylene glyco–mediated protoplast transformation system for production of fertile transgenic rice plants. Plant Physiol 93: 857–863.
Hiei Y, Ohita S, Komari T, Kumashiro T (1994) Efficient transformation of rice (*Oriza sativa* L.) mediated by Agrobacterium and sequence analysis of the boundaries of the T–DNA. Plant J 6: 271–282.

(List continued on next page.)

*Primary Examiner*—Amy J. Nelson
*Assistant Examiner*—David H Kruse
(74) *Attorney, Agent, or Firm*—Sutherland Asbill & Brennan LLP

(57) ABSTRACT

A system for transformation of maize XI12 mutant ahas2 gene into monocot (rice, corn, and wheat) cells, selection of transformed cells with the imidazolinone class of herbicide compound, and production of transgenic maize, rice and wheat plants resistant to the imidazolinone herbicides is described. The mutant ahas2 gene can be used as an effective selectable marker in transformation, useful in selection for stacked gene traits, useful as a selectable marker in breeding or hybrid seed production, and useful as a quality control tool.

19 Claims, 11 Drawing Sheets

OTHER PUBLICATIONS

Figure 1A:
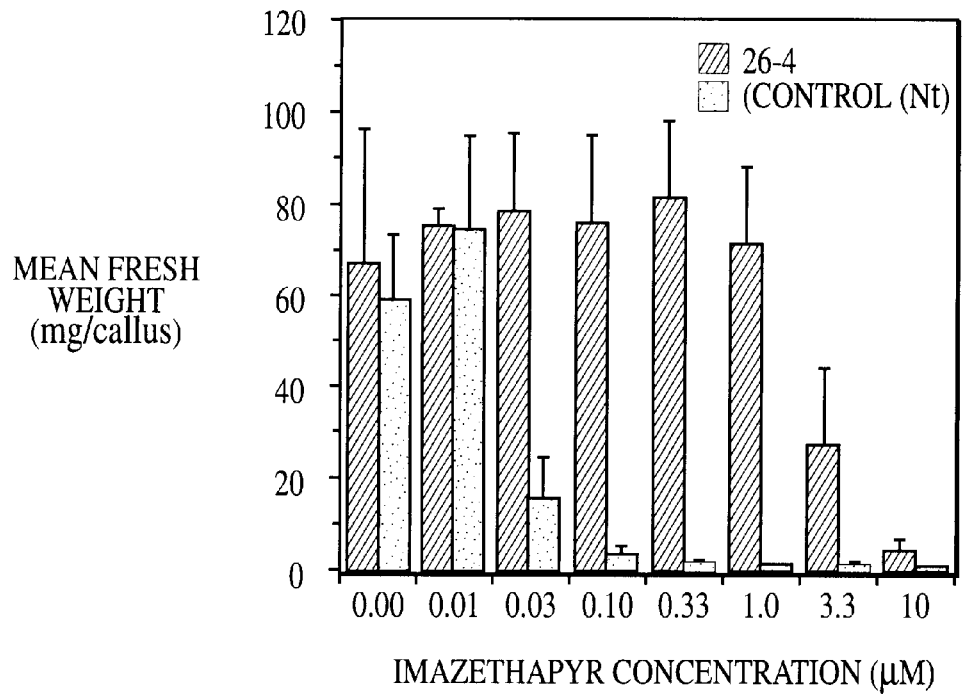

Ishida Y, Saito H, Ohta S, Hiei Y, Komari T, Kumashiro T (1996) High efficiency transformation of maize (*Zea mays* L.) mediated by *Agrobacterium tumefaciens*. Nature Biotech 14: 745–750.

Lee L, Schroll RE, Grimes HD, Hodges TK (1989) Plant regeneration from indica rice (*Oryza sativa* L.) protoplasts. Planta 178: 325–333.

Li L, Qu R, de Kochko A, Fauquet C, Beacy RN (1993) An improved rice transformation method using the biolistic method. Plant Cell Rep 12:250–255.

Li Z, Hayashimot A, Murai N (1992) A sulfonylurea herbicide resistant gene from *Arabidopsis thaliana* as a new selectable marker for production of fertile transgenic rice plants. Plant Physiol 100: 662–668.

Magha MI, Gurche P, Bregeon M, Reneard M (1993) Characterization of a spontaneous rapeseed mutant tolerant to sulfonylurea and imidazolinone herbicides. Plant Breeding 111: 132–141.

Newhouse K, Singh B, Shaner D, Stidham M (1991) Mutations in corn (*Zea mays* L.) conferring resistance to imidazolinone herbicides. Theor Appl Genet 83: 65–70.

Newhouse KE, Smith W, Starrett MA, Schaefer TJ, Singh B (1992) Tolerance to imidazolinone herbicides in wheat. Plant Physiol 100: 882–886.

Odell JT, Caimi PG, Yadav NS, Mauvais CJ (1990) Comparison of increased expression of wild–type and herbicide–resistant acetolactate synthase genes in transgenic plants, and indication of posttranscriptional limitation on enzyme activity. Plant Physiol 94: 1647–1654.

Ott KH, Kwagh JG, Stockton GW, Sidorov V, Kakefuda G (1996) Rational molecular design and genetic engineering of herbicide–resistant crops by structure modeling and site–directed mutagenesis of acetohydroxyacid synthase. J Mol Biol 263: 359–368.

Peng J, Lyznik LA, Lee L, Hodges TK (1990) Co–transformation of indica rice protoplasts with gusA and neo genes. Plant Cell Rept 9: 168–172.

Peng J, Lyznik LA, Hodges TK (1991) Co–transformation of indica rice via PEG–mediated DNA uptake. Second International Rice Genetics Symposium pp 563–574.

Peng J, Kononowicz H, Hodges TK (1992) Transgenic indica rice plants. Theor Appl Genet 83: 855–863.

Peng J, Wen F, Lister RL, Hodges TK (1995) Inheritance of gusA and neo genes in transgenic rice. Plant Molecular Biology 27: 91–104.

Rathore KS, Chowdhury VK, Hodges TK (1993) Use of bar as a selectable marker gene for the production of herbicide resistant rice plants from protoplasts. Plant Mol Biol 21: 871–884.

Sathasivan K, Haughn GW, Murai N (1991) Molecular basis of imidazolinone herbicide resistance in *Arabidopsis thaliana* var Columbia. Plant Physiol 97: 1044–1050.

Sebastian SA, Chaleff RS (1987) Soybean Mutants with Increased Tolerance to the Sulfonylurea Herbicides. Crop Sci 27: 948–952.

Sebastian SA, Fader GM, Ulrich JF, Forney DR, Chaleff RS (1989) Semidominant soybean mutation for resistance to sulfonylurea herbicides. Crop Sci 29: 1403–1408.

Shaner DL, Anderson PC, Stidham MA (1984) Imidazolinones. Potent inhibitors of acetohydroxyacid synthase. Plant Physiol 76: 545–546.

Shaner DL, Robinson PA (1985) Absorption, translocation, and metabolism of AC 252,214 in soybean (*Glycin max*), common cocklebur (*Xanthium strumarium*), and velvetleaf (*Abutilon theophrasti*). Weed Sci 33: 469–471.

Shimamoto K, Terada R, Izawa T, Fujimoto H (1989) Fertile transgenic rice plants regenerated from transformed protoplasts. Nature 338: 274–276.

Singh BK, Stidham MA, Shaner DL (1988) Assay of acetohydroxyacid synthase. Anal Biochem 171: 173–179.

Swanson EB, Herrgesell MJ, Arnoldo M, Sippell DW, Wong RSC (1989) Microspore mutagenesis and selection: canola plants with field tolerance to the imidazolinones. Theor Appl Genet 78: 525–530.

Tourneur C, Jouanin L, Vauzheret H (1993) Over expression of acetolactate synthase confers resistance to valine in transgenic tobacco. Plant Sci 88: 159–168.

Wang H, Qi M, Cutler AJ (1993) A simple method of preparing plant samples for PCR). Nucl Acids Res 21: 4153–4154.

Westerfield WW (1945) A colorimetric determination of blood acetoin. J Biol Chem 161: 495–502.

* cited by examiner

USE OF THE MAIZE X112 MUTANT AHAS 2 GENE AND IMIDAZOLINONE HERBICIDES FOR SELECTION OF TRANSGENIC MONOCOTS, MAIZE, RICE AND WHEAT PLANTS RESISTANT TO THE IMIDAZOLINONE HERBICIDES

The present application claims priority from U.S. provisional application Ser. No. 60/200,658, filed Apr. 28, 2000.

FIELD OF THE INVENTION

The present invention relates, specifically, to the transformation of maize X112 mutant ahas 2 gene into monocots such as maize (corn), wheat and rice, selection of transformed maize (corn), rice and wheat cells with imidazolinone, production of transgenic maize (corn), rice and wheat materials and plants resistant to the imidazolinone herbicides, in vitro characterization of the transformed plants, and greenhouse performances of imidazolinone resistant transgenic maize (corn), rice and wheat plants treated with various herbicides.

BACKGROUND OF THE INVENTION

The existence of the branch chain amino acid (valine, leucine and isoleucine) biosynthetic pathway in plants, and its absence in animals is one of the major differences of plant and animal biochemistry. Therefore, inhibition of the branch chain amino acid biosynthesis is detrimental to plants but has no effect on animals. Imidazolinone and sulfonylurea herbicides inhibit, acetohydroxyacid synthase (AHAS, or acetolactate synthase—ALS; E.C.4.1.3.18), the key enzyme in the biosynthesis of branch chain amino acids (Chaleff and Mauvais, 1984; Shaner et al. 1984). Consequently, because imidazolinone and sulfonylurea herbicides are effective at very low application rates, and relatively non-toxic to animals, they are widely used in modern agriculture.

The differential sensitivity to the imidazolinone herbicides is dependent on the chemical nature of the particular herbicide and differential metabolism of the compound from toxic to non-toxic form in the plants (Shaner et al. 1984; Brown et al. 1987). Other plant physiological differences such as absorption and translocation also play an important role in selectivity (Shaner and Robinson 1985). Computer-based modeling of the three dimensional conformation of the AHAS-inhibitor complex predicts several amino acids in the proposed inhibitor binding pocket as sites where introduced mutations would likely confer selective resistance to imidazolinones (Ott et al. 1996). Transgenic plants produced with these rationally designed mutations in the proposed biding sites of the AHAS enzyme exhibited specific resistance to a single class of herbicides (Ott et al. 1996).

Application of imidazolinone herbicides in field production of major crops enables more effective weed control and less environmental impact than other chemicals. Among the major agricultural crops, only soybean is naturally resistant to imidazolinone herbicides due to its ability to rapidly metabolize the compounds (Shaner and Robinson 1985) while others such as corn (Newhouse et al. 1991), wheat (Newhouse et al. 1992) and rice (Barrette et al. 1989) are somewhat susceptible. In order to extend the application of imidazolinone and sulfonylurea herbicides to more crops, it is necessary to enhance plant resistance to these compounds. To date, three major approaches have been used to enhance plant resistance: 1) screening for spontaneous resistant mutations in cell culture (Chaleff and Ray 1984; Anderson and Georgeson 1989; Sebastian et al. 1989; Magha et al. 1993), 2) artificially inducing mutations in seeds or microspores (Swanson et al. 1989; Newhouse et al. 1992; Croughan 1996), and 3) transferring resistance genes between different species by genetic engineering (Haughn et al. 1988; Charest et al. 1990; Odell et al. 1990; Li et al. 1992; Tourneur et al. 1993). Thus far spontaneous herbicide resistant mutants have been identified and characterized in tobacco (Chaleff and Ray 1984), soybean (Sebastian et al. 1989), corn (Anderson and Georgeson 1989) and rapeseed (Magha et al. 1993). Chemical mutagenesis successfully produced resistant mutants in wheat (Newhouse et al. 1992), canola (Swanson et al. 1989) and rice (Croughan 1996). Studies on tobacco (Haughn et al. 1988; Odell et al. 1990; Charest et al. 1990) and rice (Li et al. 1992) suggested the potential of transferring genes from one species to another for the production of resistant crops.

Advances in transformation technologies of monocots, especially of rice have made possible the transfer of genes between species for development of transgenic plants with improved characteristics. Transgenic rice plants have been produced by transformation of protoplasts (Shimamoto et al. 1989; Peng et al. 1990), bombardment of cells (Christou et al. 1991; Li et al. 1993), and more recently, Agrobacterium-mediated transformation of immature embryos (Chan et al. 1992; Hiei et al. 1994; Aldemita et al. 1996). Critical in all the transformation processes is the ability to select for the cells that have been transformed over the rest of the population of cells. Typically a combination of an antibiotic and a gene conferring resistance to the antibiotic has been used. Examples include the neomycin phosphotransferase (neo) gene for resistance to kanamycin or genetic (G-418), hygromycin B transferase (hyh) for hygromycin B resistance (Shimamoto et al. 1989; Hayashimoto et al. 1990), and the bar gene for phophinothricin resistance (Christou et al. 1991; Rathore et al. 1993). All of these selectable genes (neo, hyh and bar) are of bacterial origin. In one report, use of a mutant als gene from Arabidopsis coupled with selection on sulfonylurea herbicide was demonstrated for production of transgenic rice plants (Li et al. 1992). An increase in in vitro resistance to chlorsulfuron of similar magnitude (200-fold) was demonstrated in transgenic rice containing 35S/als transgene (Li et al. 1992), and imidazolinone-resistant growth of transgenic tobacco was reported to be 100-fold greater than nontransformed control plants (Sathasivan et al.1991). In the literature, expression of the introduced AHAS (or ALS) gene at different magnitudes was achieved by manipulating several aspects of the transformation that included the use of different promoters and screening larger populations of transformants (Odell et al. 1990; Sathasivan et al. 1991; Li et al. 1992). Studies showed that replacing the Arabidopsis ALS promoter with the CaMV35S promoter resulted in 40-fold differences in in vitro resistance to chlorsulfuron (Li et al. 1992). In tobacco, increase in resistance to imazethapyr in individual calli transformed with mutant als gene from Arabidopsis ranged from 10- to 1000-fold, most likely reflecting the differences in gene copy numbers or in chromosomal positions of the transgenes (Sathasivan et al. 1991).

Imidazolinone-specific resistance has been reported in a number of patents. U.S. Pat. No. 4,761,373 described in general terms an altered ahas as a basis of herbicide resistance in plants, and specifically disclosed certain imidazolinone resistant corn lines. U.S. Pat. No. 5,013,659 disclosed that mutants exhibiting herbicide resistance possess mutations in at least one amino acid in one or more conserved regions. The mutations described therein encode either cross-resistance for imidazolinones and sulfonylureas or sulfonylurea-specific resistance but no imidazolinone-specific resistance. Additionally, U.S. Pat. No. 5,731,180 and continuation-in-part U.S. Pat. No. 5,767,361 isolated a gene encoding imidazolinone-specific resistance in a monocot and determined it to be associated with a single amino acid substitution in a wild-type moncot AHAS amino acid sequence. U.S. Pat. Nos. 5,731,180 and 5,767,361, as well as U.S. Pat. Nos. 5,750,866 and 6,025,541, are incorporated herein by reference. However, while the referenced patents generally allude to the use of the gene as a selectable marker for selection on imidazolinone, the present invention describes the specific application of the maize X112 mutant ahas 2 gene to monocots such as maize (corn), rice and wheat varieties, or use of the mutant XI12 ahas 2 gene as a selectable marker coupled with a imidazolinone compound as a selection system for resistance to the imidazolinone herbicides.

The AHAS gene codes for acetohydroxyacid synthase (AHAS, E.C.4.1.3.18; also called acetolactate synthase; ALS) which is the first common enzyme in the biosynthetic pathway of branch chain amino acids (Shaner et al. 1984). The imidazolinone herbicides are a class of herbicides that inhibit AHAS activity thus, preventing further growth and development of susceptible plants such as rice and many weed species. In biochemical studies, selectivity of the imidazolinone herbicides has been shown to be based on differences in nature and rate of metabolism of the herbicides (Shaner and Robinson 1985; Brown et al. 1987). In genetic studies, mutations in the ahas gene have been linked for resistance to the imidazolinone herbicides in canola (Swanson et al. 1989) and corn (Newhouse et al. 1991). Analysis of the mutant ahas 2 gene, isolated from maize (XI12) plants revealed that a single base mutation from G to A at nucleotide 621 relative to the initiation codon resulted in a one amino acid change in the AHAS enzyme from Ser to Asn (Dietrich, 1998). The term mutant ahas 2 gene as used herein includes any additions, deletions, or substitutions in the nucleic acid sequence as described in Dietrich, U.S. Pat. No. 5,731,180, that do not change the function of the mutant ahas 2 gene. The function of the mutant ahas 2 gene is to confer resistance to imidazolinone herbicides. The maize XI12 mutant ahas 2 gene presents a number of advantages for use in plant transformation. It is a plant gene and even this mutant form is known to exist in plant populations. A combination of the maize XI12 mutant ahas 2 gene and imidazolinone chemistry provides a useful system for selection of transformed cells, plants and progeny. Use of a plant mutant ahas gene for selection in plant transformation circumvents the problems associated with transformation of antibiotic gene of bacterial origin in transgenic plants. The term mutant ahas 2 gene as used herein includes any additions, deletions, or substitutions in the nucleic acid sequence as described in Dietrich, U.S. Pat. No. 5,731,180, that do not change the function of the mutant ahas 2 gene. The function of the mutant ahas 2 gene is to confer resistance to imidazolinone herbicides.

BRIEF SUMMARY OF THE INVENTION

In this invention we report the transformation of maize X112 mutant ahas 2 gene into maize and wheat embryos and rice protoplasts, selection of transformed cells with an imidazolinone compound, production of transgenic maize, rice and wheat plants resistant to the imidazolinone herbicides, in vitro characterization of the transformed plants, and greenhouse performances of imidazolinone resistant transgenic plants treated with various herbicides.

In rice, resistant calli were recovered from transformations following selection on imazethapyr and regenerated into fertile plants. Genetic study on two transgenic rice lines (26 and 29) showed that the introduced maize ahas2 gene was stably transmitted to progeny plants and conferred a single dominant trait inherited in a Mendelian fashion. Homozygous imidazolinone resistant lines were readily identified and isolated based on seed germination and greenhouse screen tests. A 100-fold increase in in vitro resistance to imazethapyr in cell lines and immature embryos derived from transgenic homozygous resistant plants was demonstrated. Also the invention can be used to deliver a second gene in co-transformation. Also, the invention identifies the production of transgenic maize and wheat plants by Agrobacterium-mediated transformation using the maize X112 mutant ahas2 gene as a selectable marker coupled with selection of callus material and regeneration of plants on media supplemented with the imidazolinone herbicides. Transformation efficiency averaged about 2% and reached to as high as 16%–20% in some experiments for corn and ranged from 0.4 to 3.1% for wheat.

We evaluated performances of transgenic maize, rice and wheat plants containing the maize XI12 ahas 2 gene in response to applications of various herbicides in greenhouse. A total of 9 herbicides including five imidazolinones (PURSUIT® imazethapyr, CADRE® imazameth, RAPTOR® imazamox, SCEPTER® imazaquin, and ARSENAL® imazapyr, two rice herbicides, AC322,140 cyclosufamuron and LONDAX® bensulfuron-methyl, ACCENT® nicosulfuron and CLASSIC® clorimuron-ethyl applied at 4 different rate were used in a study of transgenic rice plants. The results showed that transgenic plants were resistant to the five imidazolinone herbicides at rates as high as 6× typical use rates and retained sensitivity to the sulfonylurea herbicides as compared to untransformed control plants. When treated with herbicides, transgenic plants produced yields comparable with their untreated counterparts. Untransformed control plants, however, had 10 to 20% higher yields than transgenic plants in the absence of herbicide treatments. All herbicides at all rates tested had no detrimental effects on seed set, except higher rates of ARSENAL® imazapyr caused severe sterility in transgenic plants. Enzyme assays provided evidence that the introduced XI12 maize ahas 2 gene conferred selective resistant AHAS enzyme in the transgenic plants. Evaluation of effects of different imidazoline herbicides on transgenic corn plants showed there was no injury up to 16×ARSENALO® imazapyr (384 g/ha), 8×PURSUIT® imazethapyr (500 g/ha), 4×CADRE® imazameth (800 g/ha). At 4×imazamox (160 g/ha), no or slight injury to the plants was observed. An increase of 5× tolerance to imazamox was demonstrated in transgenic wheat plants. The mutant ahas2 gene can be used as an effective selectable marker in transformation, useful in selection for stacked gene traits, useful as a selectable marker in breeding or hybrid seed production, and useful as a quality control tool.

BRIEF DESCRIPTION OF THE FIGURES/DRAWINGS

Figure legends

FIG. 1. Fresh weight of suspension cells (A) and calli (B) derived from immature embryos of transformed (26-4) and untransformed control (Nt) plants on media amended with various concentrations of imazethapyr.

Figure 2A:
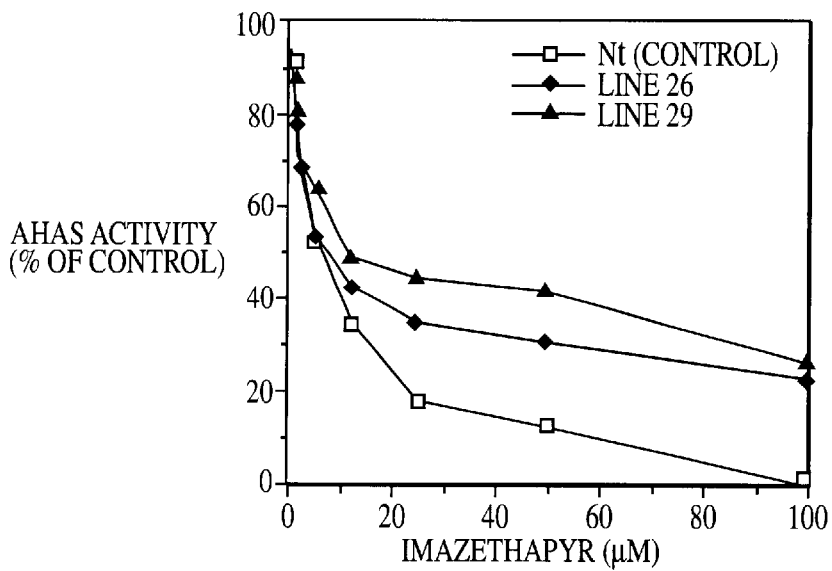
Figure 2B:
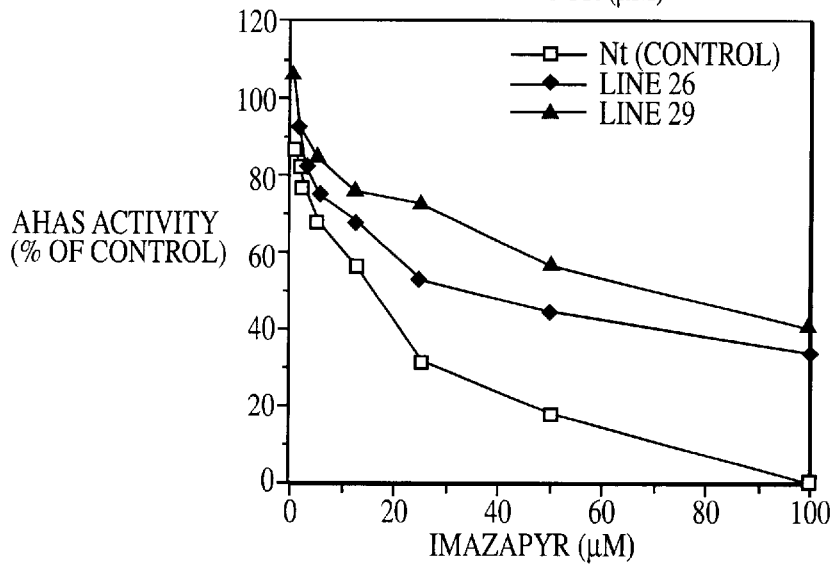
Figure 2C:
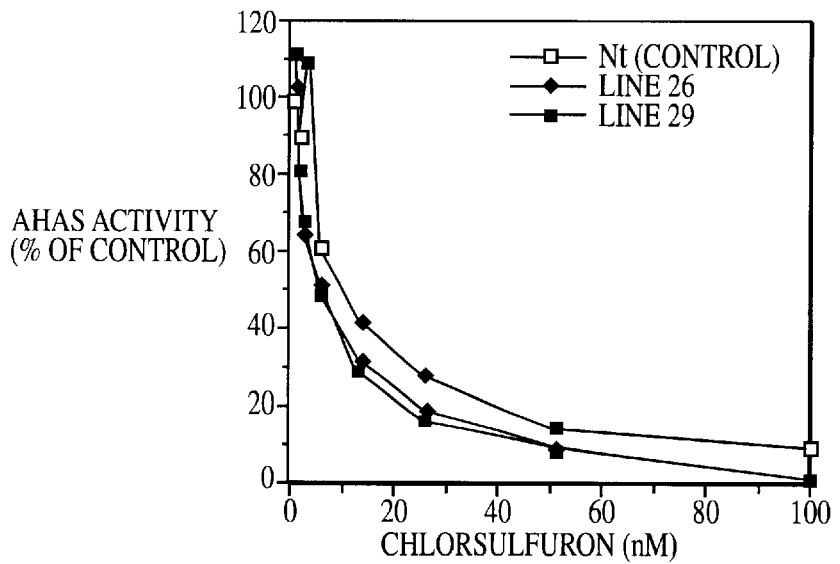
Figure 3A:
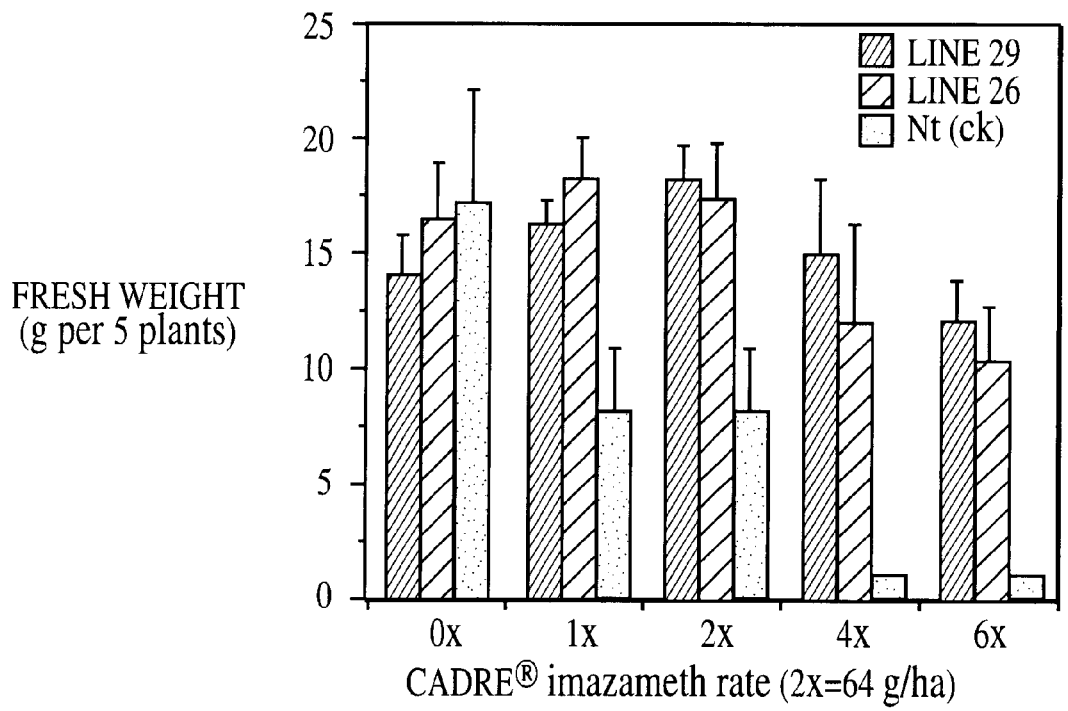
Figure 3B:
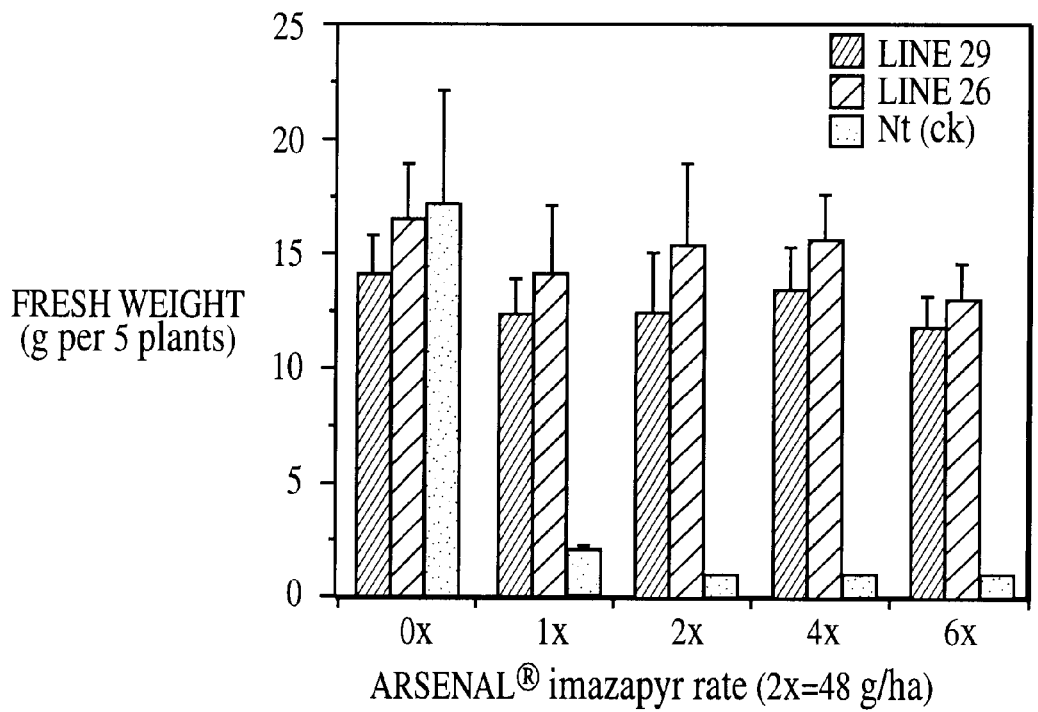
Figure 3C:
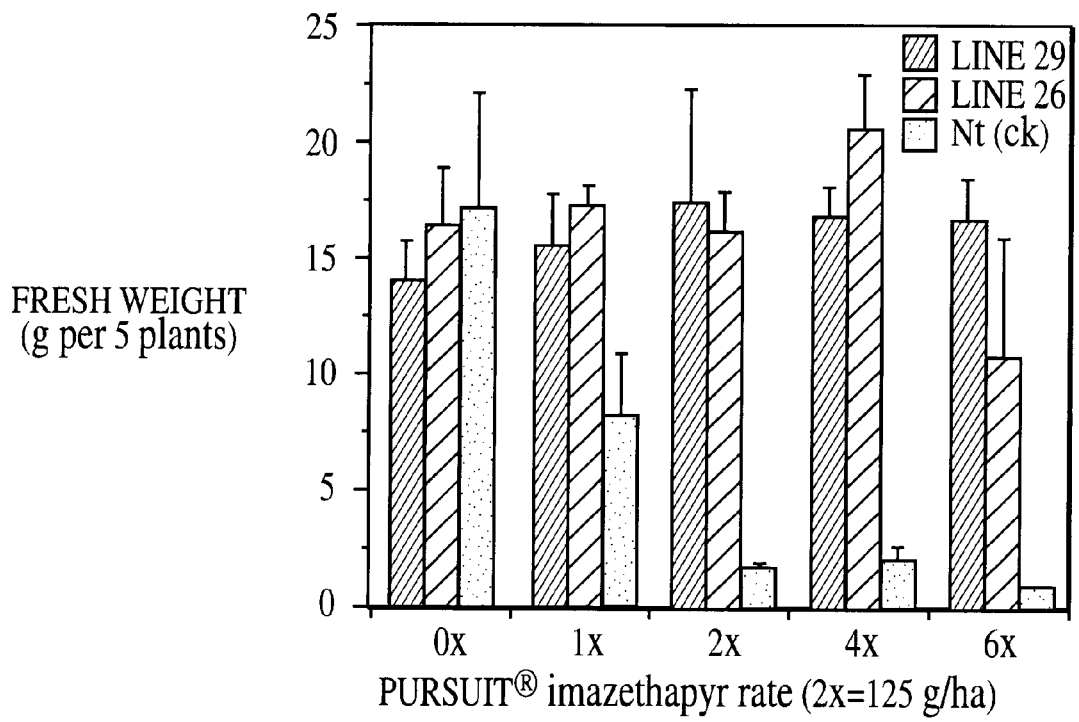
Figure 3D:
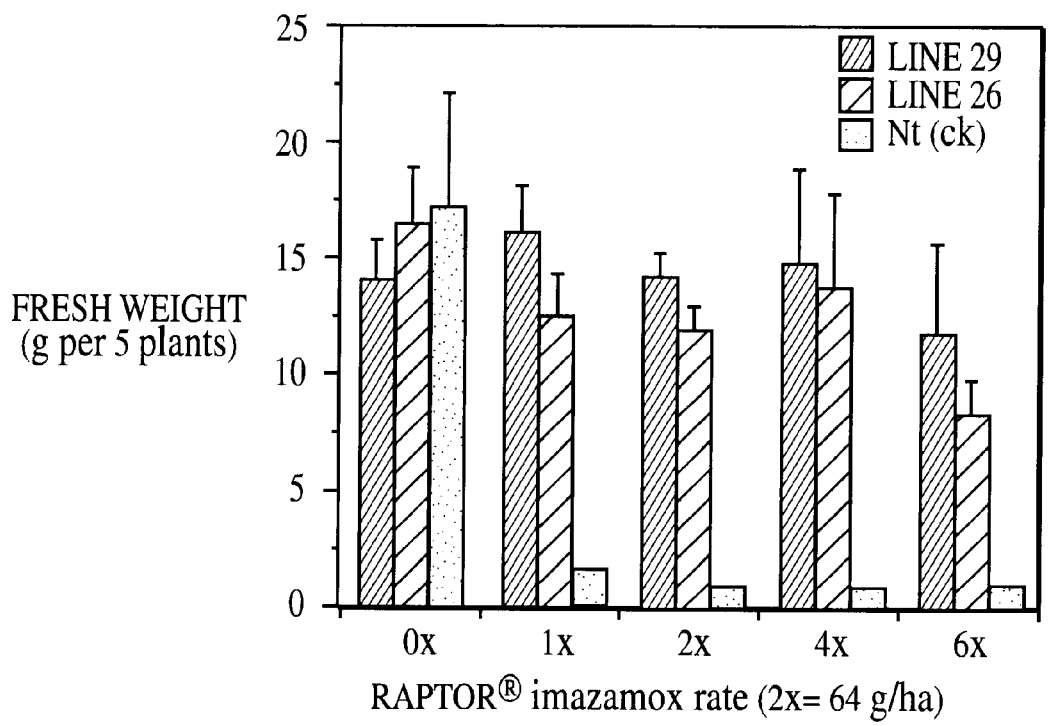
Figure 3E:
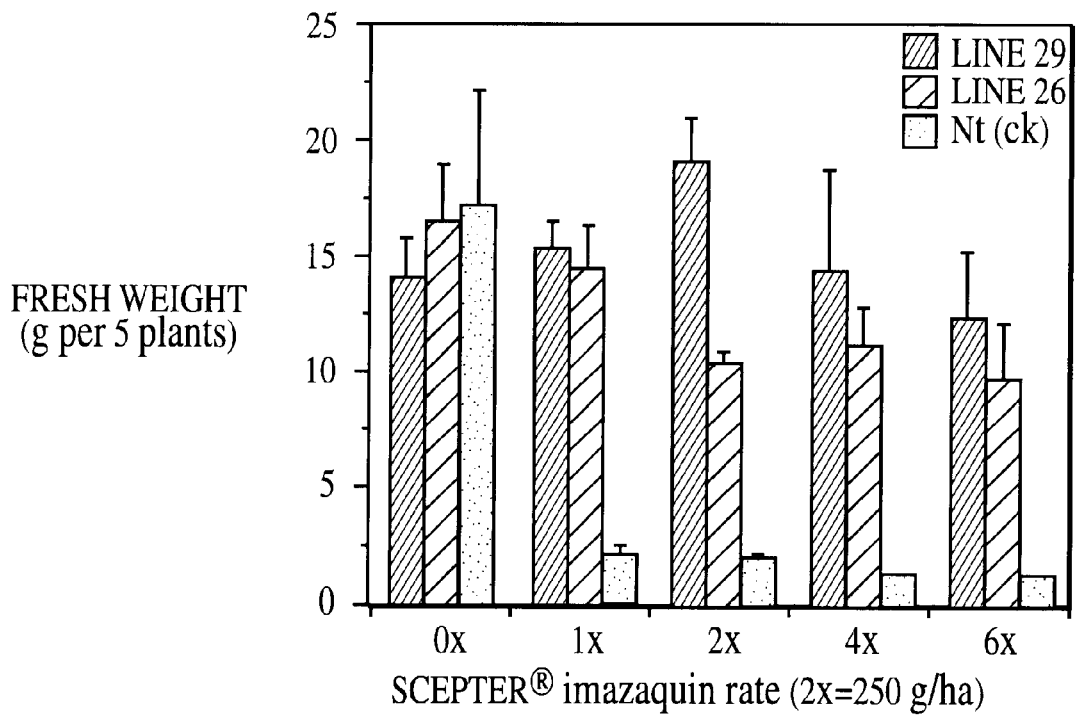
Figure 3F:
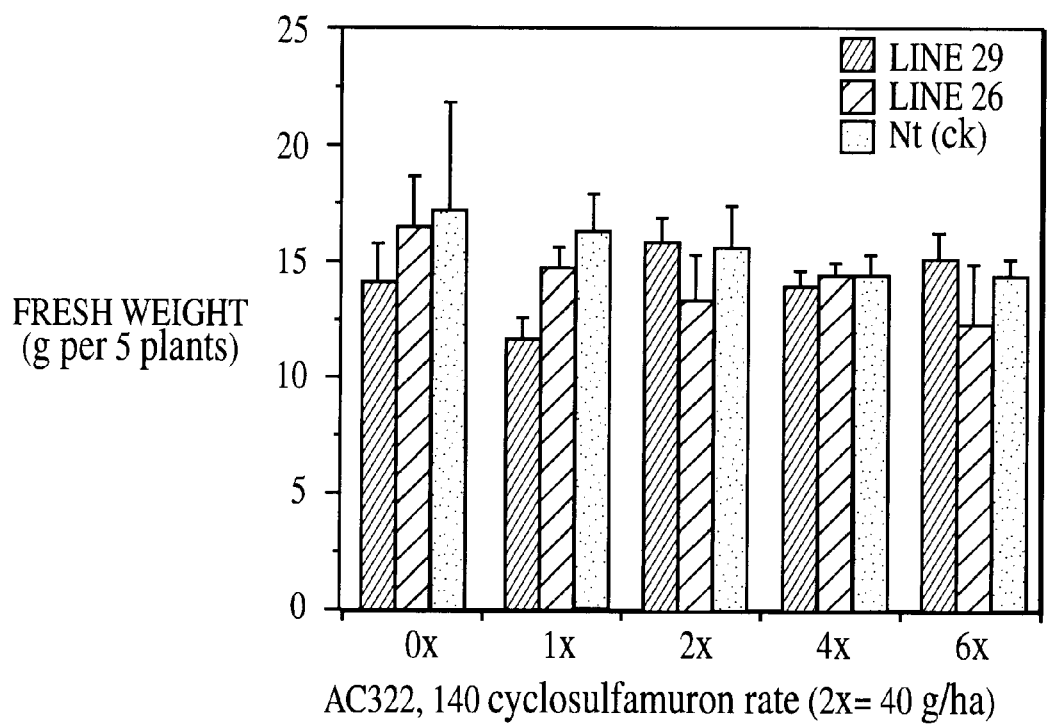
Figure 3G:
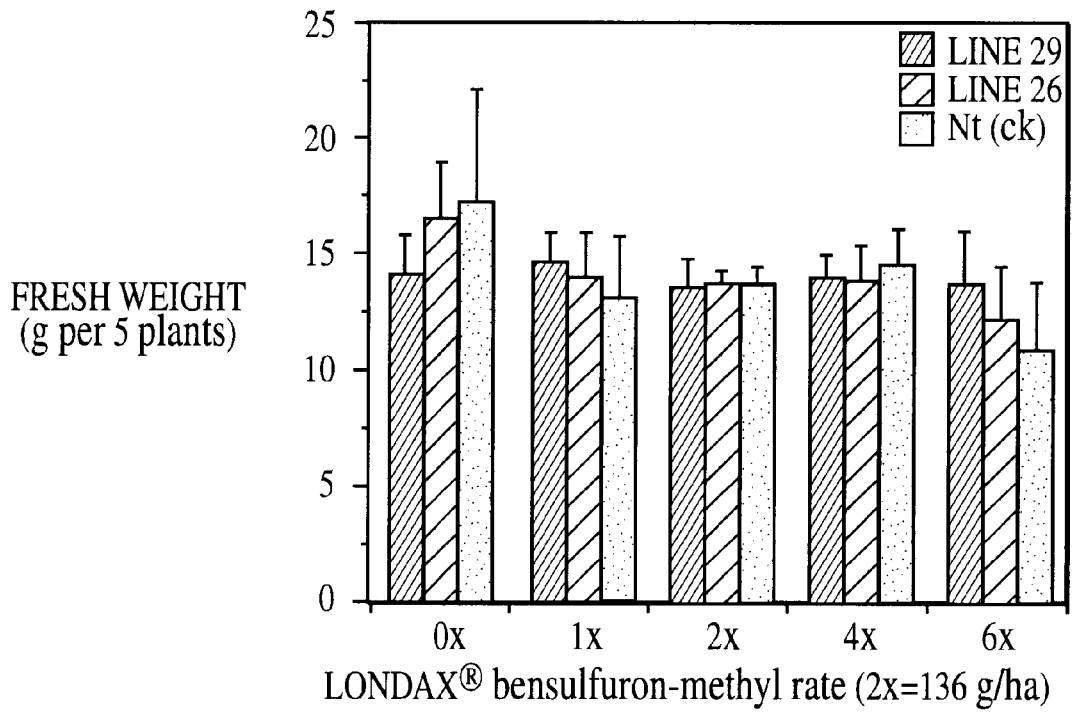
Figure 3H:
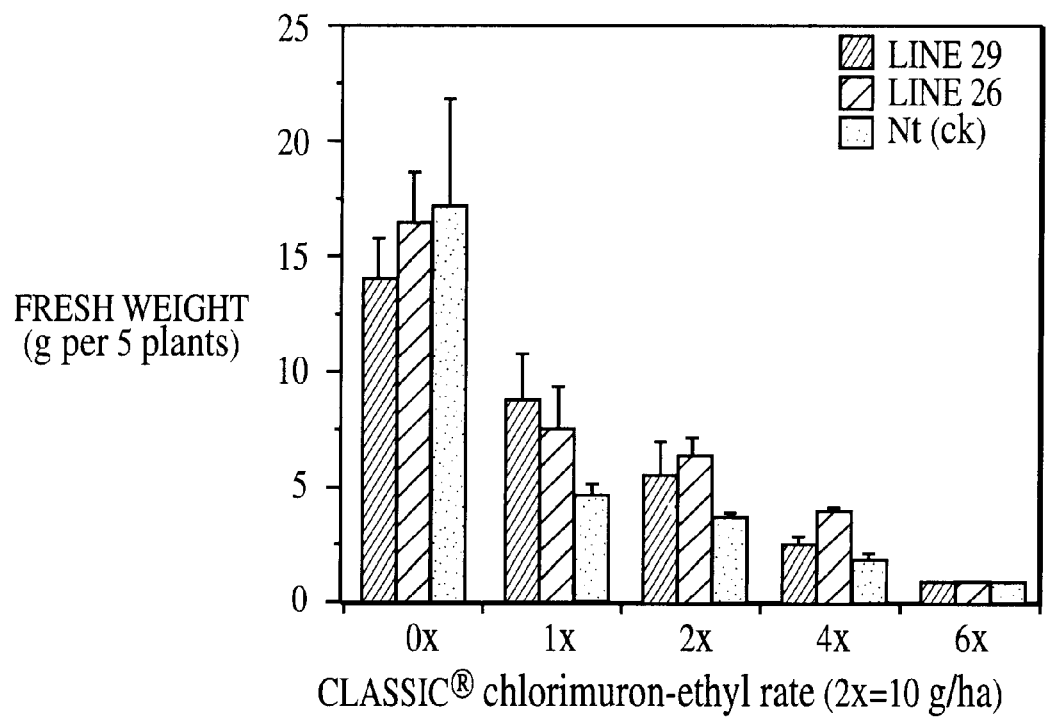
Figure 3I:
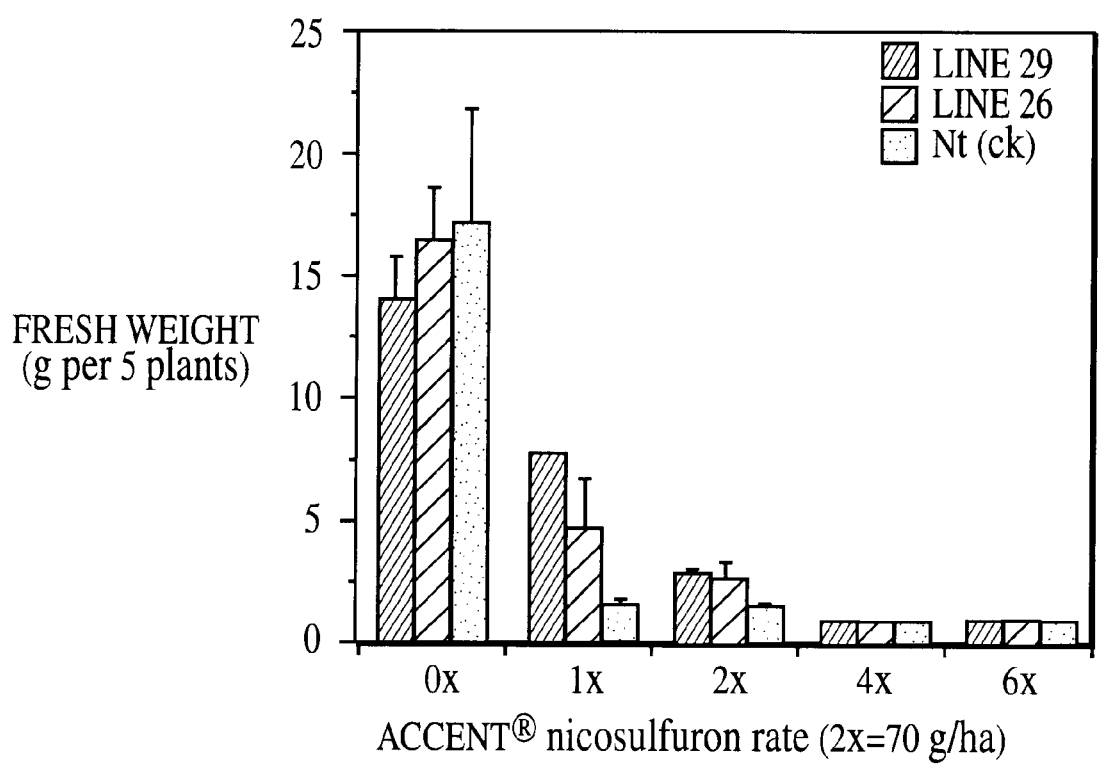

FIGS. 2A–C. Enzyme assay for AHAS activity. Nt is untransformed control and Lines 26 and 29 are transgenic rice plants.

FIGS. 3A–I. Effect of different herbicides on fresh weight of rice plants. Herbicides were sprayed at three-leaf stage (post-emergence) at 1, 2, and 4× rates indicated in each graph. Lines 26 and 29 are transgenic plants and Nt is untransformed control.

Figure 4A:
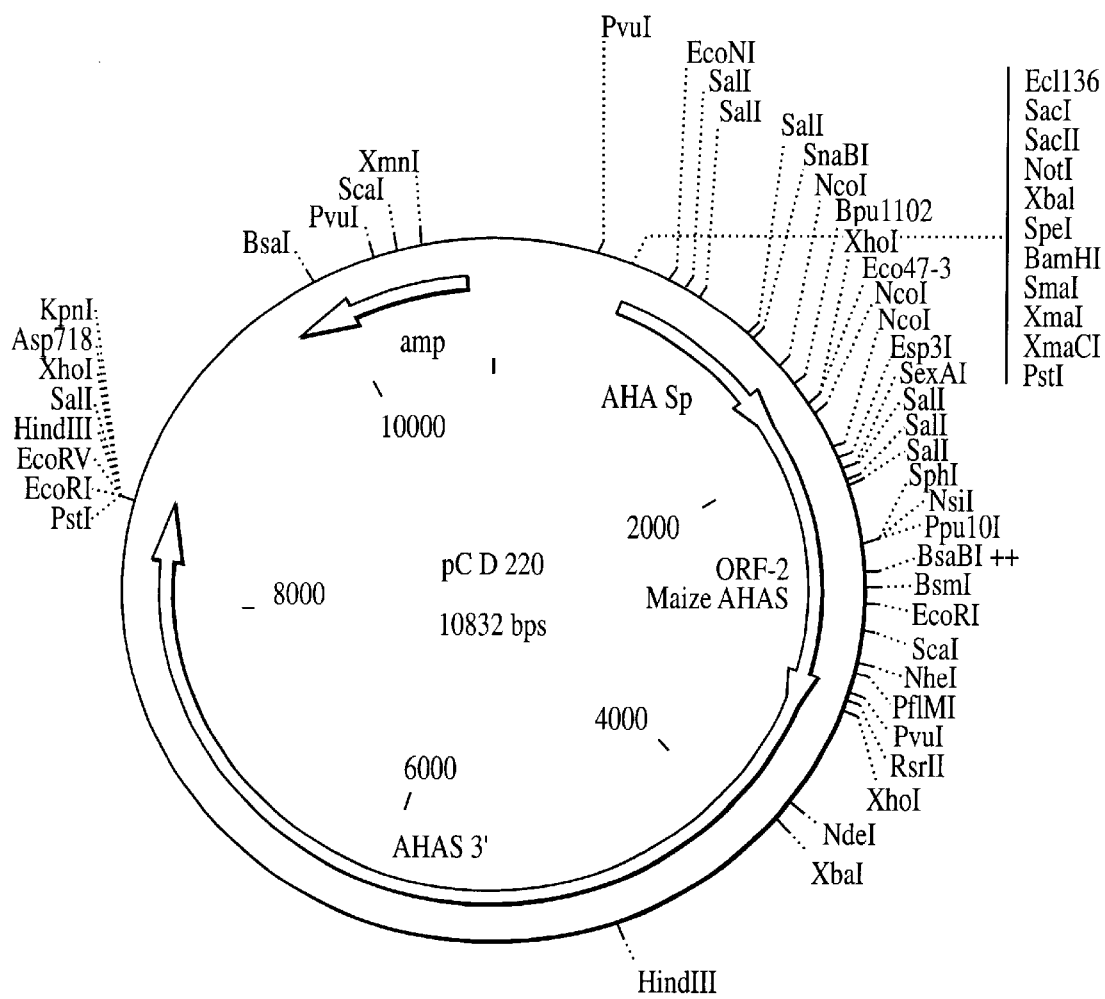
Figure 4B:
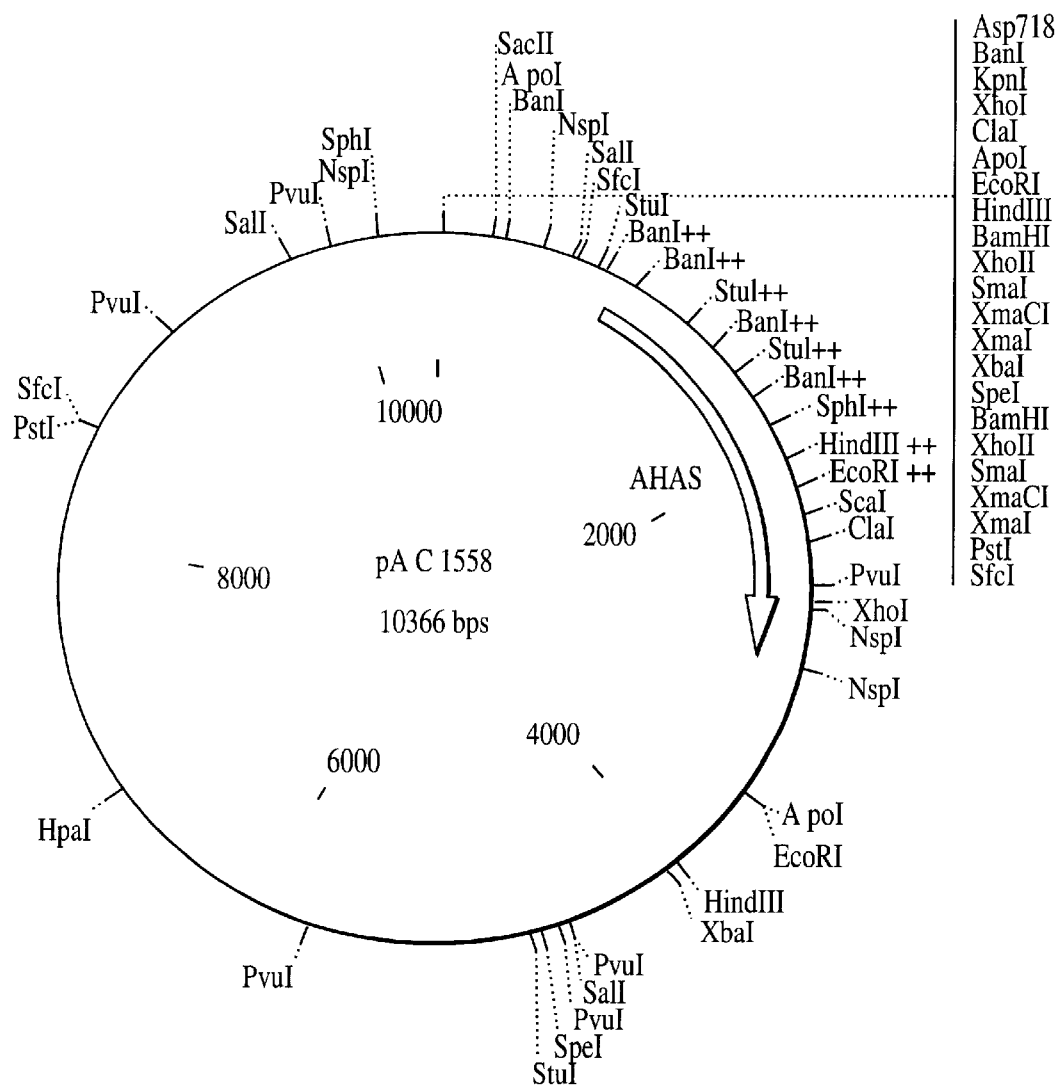

FIGS. 4A–B. Plasmid constructs used in transformation.

Figure 5:
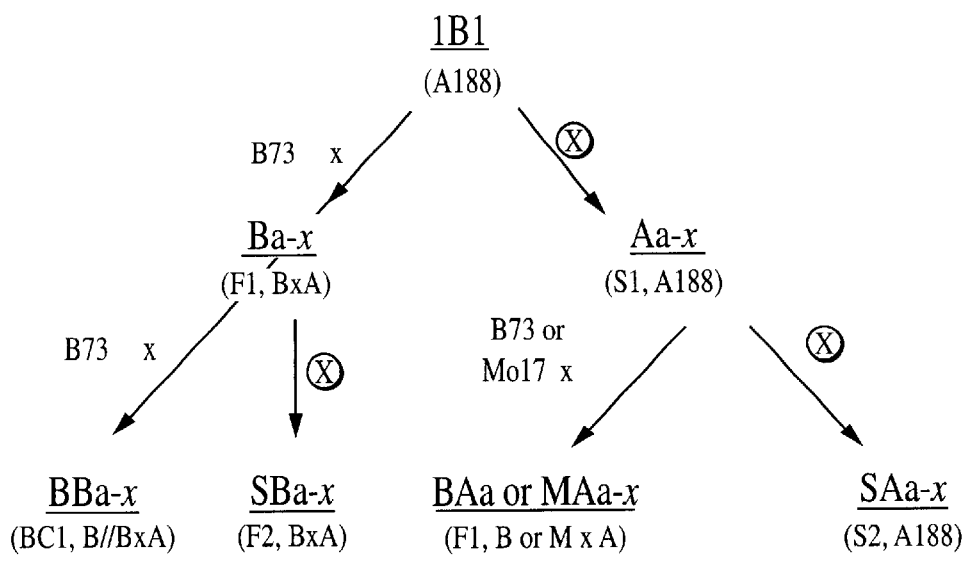

FIG. 5. Crossing scheme for transgenic corn

Figure 6A:
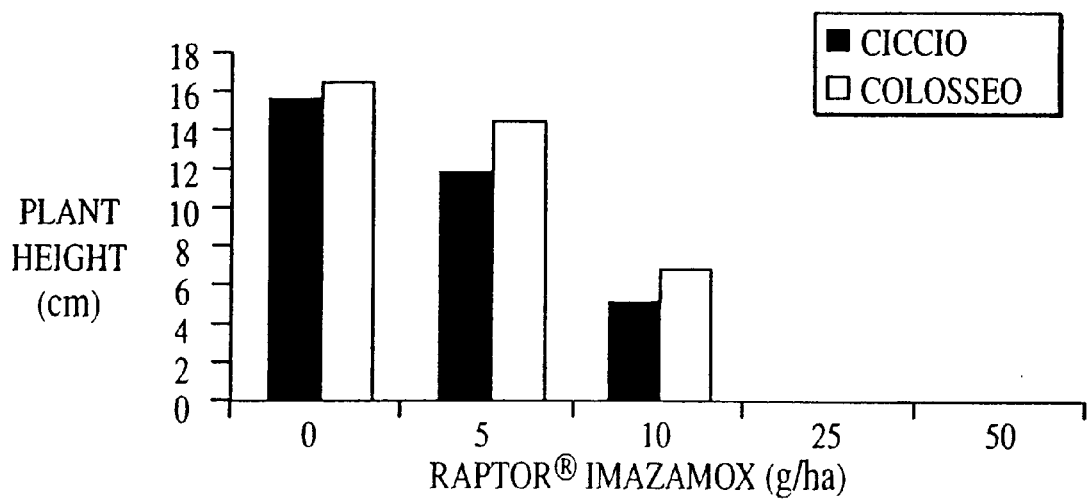
Figure 6B:
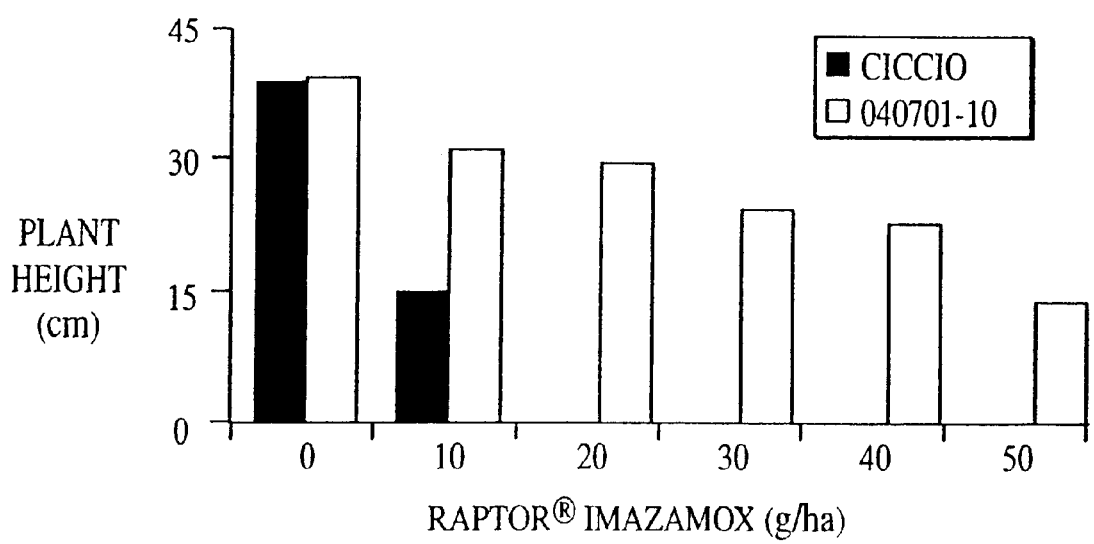

FIG. 6. Effect of imazamox on plant height of transformed and non-transformed wheat plants. Plant height of non-transformed Ciccio and Closseo plants (FIG. 6A) when treated with 0 to 50 g/ha imazamox. Transgenic line 040701-10 and non-transformed Ciccio treated with 0 to 50 g/ha imazamox at three-leaf stage (FIG. 6B).

DESCRIPTION OF THE INVENTION

In a preferred embodiment, transgenic rice plants are produced by transformation with the maize XI12 mutant ahas 2 gene, which is then utilized as a selectable marker. Rice protoplasts isolated from rice varieties Nortai (Nt) and Radon (Rd) were transformed with pCD220, a plasmid construct containing the maize X112 ahas promoter and mutant X112 ahas 2 gene (Ser621Asn), via PEG mediated transformation. The transformation efficiency in the present study was slightly lower than but similar with those reported for other resistant gene/selection systems used for rice (Peng et al. 1990, Li et al. 1992). In tobacco, recovery of transformants from chlorsulfuron (a herbicide with mode of action similar to that of imidazolinone herbicides) was also reported to be much lower than recovery of transformants from kanamycin (Charest et al. 1990). Unlike antibiotics such as kanamycin (Peng et al. 1991), the imidazolinone herbicide did not have a detrimental effect on the plant regeneration potential of the transformed rice calli. Therefore, coupling of the maize mutant ahas2 gene with selection on imidazolinone herbicides presents another valuable selectable gene and selection system for genetic engineering of rice and other monocots.

Also, in further embodiments, the invention identifies transgenic maize and wheat plants produced by Agrobacterium-mediated transformation using the maize X112 mutant ahas 2 gene as a selectable marker. In particular, immature embryos, 0.8 to 1.5 mm., were isolated at 10 to 16 days after pollination and co-cultivated with Agrobacterium cells harboring the maize X112 mutant ahas 2 gene for 3–7 days. Explants were then transferred to selection medium containing the imidazolinone herbicides for 7–10 weeks for wheat and 5–8 weeks for maize and subcultured every 2–3 weeks. In our selection scheme, the initial concentration of the imidazolonone herbicides was very low, only 0.05 to 0.1 μM imazethapyr or imazamox was added to medium. We found it was critical to keep the selection pressure low in the beginning to assure formation of regenerable callus cells. When high concentration of the imidazolinone compounds was used in the initial selection stage, only slimy callus that could not regenerate into plants was formed. During the second and third selection stages, concentrations of imazethapyr or imazamox were increased to 0.5 or 0.3 μM, respectively. Most cells that grew normally at these concentrations were transformed with the maize mutant XI12 ahas 2 gene. Concentration of imazethapyr was lowered to 0.25 μM during maize shoot regeneration and no imidazolinoe compound was added during root formation. During wheat regeneration, concentration of imazamox was 0.1 μM and no selection reagent during root formation either.

Putative transgenic plants were then sprayed with imidazolinone herbicides. Wheat plantlets were sprayed with 25–50 g/ha RAPTOR® at 10–14 days after transplanting and corn plants were sprayed with 125 to 250 g/ha PURSUIT® imazethapyr about two weeks after transplanting. Plants survived the herbicide treatments were transplanted to larger pots and grown to maturity.

Transgenic maize and wheat plants produced from these transformation systems contained the introduced maize X112 mutant ahas 2 gene. PCR (Polymerase Chain Reaction) and/or Southern blot analysis was used to confirm presence of the transgene. Southern blot analysis of DNA extracted from plants (putative transformants) regenerated from imazethapyr resistant calli showed that all the plants assayed had the introduced maize ahas 2 gene. Some of the plants received multiple copies with multiple insertions and others were transformed with one to two copies of the gene integrated into a single locus. Plants that had single integration patterns, with one to two copies of the intact transgenes were carried to subsequent generations for further evaluation in vitro and in vivo. Transmission of the transgene to rice T1 plants were studied by PCR analysis and spray tests.

Three tests were performed to evaluate herbicide resistance of T2 progeny of transgenic rice. T2 progeny were first evaluated by a seed germination test followed by the greenhouse spray test and PCR analysis. As a prelude to testing the transgenic plants, an experiment was conducted to germinate untransformed rice seeds at imazethapyr concentrations ranging from 0.1 to 10 μM. Untransformed seeds were completely inhibited at 1 μM; therefore 5 μM imazethapyr, equivalent to 5 times the threshold, was used for subsequent seed germination tests of the T2 generation. The greenhouse spray test and PCR analysis were used to further confirm the results of the seed germination test with consistent identification of lines as resistant homozygous, susceptible homozygous or segregating hemizygous.

Data obtained from characterization of the transformed cells and plants as shown the examples show that transgenic maize, wheat and rice produced according to the invention have sufficient resistance at plant level. Rice is naturally susceptible to the imidazolinone herbicides in vitro. Very low concentrations (0.1 μM and higher) of imazethapyr inhibit the growth of untransformed rice cells. Transgenic cells with the introduced maize XI12 mutant ahas 2 gene exhibited a 100-fold increase in resistance to imazethapyr in vitro in both fine suspension cells or freshly isolated immature embryos derived from the transgenic plants.

In vitro AHAS assays were performed to demonstrate that the resistant AHAS enzyme was the basis of selective herbicide tolerance in the transgenic plants. Previously published procedures were used for the extraction and in vitro assay for AHAS activity (Singh et al. 1988). Lower portions of the shoots were used as the source of plant tissue for the assay. The desalted crude extracts were used for the in vitro enzyme assays. Acetolactate produced by the enzyme was converted to acetoin, which was measured by the Westerfield assay system.

The present invention further provides for fertile transgenic plants, which were morphologically normal and transmitted and inherited the transgenes. The regenerated plants had morphological traits that closely resembled their seed-grown counterparts and were mostly self-fertile although some plants had very low seed set. Production of viable seed and inheritance of the transgene permits transmission of the herbicide resistance from transgenic lines to other elite breeding lines.

Finally, the examples show the greenhouse performances of imidazolinone resistant transgenic plants treated with various herbicides. The results of greenhouse evaluation on performances of transgenic plants containing the maize XI12 mutant ahas 2 gene presented here is very encouraging. Transgenic rice and maize plants so produced can be used in field production to sustain application of herbicide with minimum damage to the crop. The two varieties of wheat Ciccio and Colosseo used for our transformations are extremely sensitive to the imidazolinone herbicides, especially to RAPTOR® imazamox. When treated with 10 g/ha (~⅓ field application rate), plant heights of Ciccio and Colosseo were reduced to 50% less than those of transformed plants having the mutant maize X112 ahas gene. Plants were completely killed when sprayed with more than 10 g/ha RAPTOR® imazamox. The present invention further provides for transgenic wheat plants with elevated resistance to the imidazolinone herbicide.

EXAMPLES OF PREFERRED EMBODIMENTS

Example 1

Plasmid Constructs Used for Transformation

The following plasmids are used for monocot transformation (see FIG. 4).

pCD220

The plasmid pCD220 contains the maize ahas promoter driving the maize XI12 mutant ahas 2 gene and its native terminator. The pCD220 plasmid was constructed by subcloning the XI12 ahas 2 gene as a Pst I fragment into pBluescript II (pKS-) (pKS- was purchased from Stratagene, 11011 North Torrey Pines Rd. La Jolla, Calif. 92037).

pAC1558

This plasmid is made by insertion of an XbaI fragment of pCD220 into JT vector pSB12 and integrated into pSB1 (pSB12 and pSB1 are vectors from Japan Tobacco Inc, see U.S. Pat. No. 5,591,616, American Cyanamid has a license to use these vectors). It contains the maize ahas promoter driving the maize XI12 mutant ahas2 gene and its native terminator.

Example 2

Rice Transformation and Selection, and Characterization of Transgenic Rice for Resistance to the Imidazolinone Herbicides Protoplasts were isolated from rice varieties Nortai (Nt) and Radon (Rd) suspension cells that are gift of Dr, Thomas K. Hodges (Department of Botany and Plant Pathology, Purdue University, W. Lafayette, Ind. 47907) and transformed according to procedures described by Peng et al (1990, 1992). The construct (pCD220) used for the transformation, as described in Example 1, contained the mutant maize XI12 ahas2 gene (Ser621 Asn) driven by its own promoter. After transformation, the protoplasts were either cultured on Millipore filters placed on top of solid agarose medium containing feeder cells (Lee et al. 1989). The agarose used for rice culture had gelling temperature 36–42° C., and was purchased from GIBCOBRL (Grand Island, N.Y. 14702). Alternately, the protoplasts were embedded in alginate films by mixing 1 volume of protoplast with 1 volume of 3% alginate in 7% glucose solution and cultured in the same protoplast culture medium as described above (Peng et al., 1990, 1992) with feeder cells but in liquid form. The alginate cultures were maintained in the dark on a slow shaker (40–50 rpm). The media are not critical to the process and can be varied according to the knowledge of those skilled in the field. In the agarose culture, selection for transformed cells started three weeks after transformation on 0.5 $\mu$M imazethapyr (AC263,499) and continued for 6 to 8 weeks with one or two subcultures in-between. When the alginate/liquid culture method was used, selection began 3–5 days after transformation on 0.5 $\mu$M imazethapyr and the cultures were transferred to fresh liquid medium containing 0.5 to 1 $\mu$M imazethapyr every 7 to 10 days. Seven to nine weeks after transformation, resistant colonies (about 0.5 mm in size) were picked up and placed onto LS medium (Linsmaier and Skoog, 1965) supplemented with 0.5 mg/l 2,4-D, 2% sucrose, and 0.6% agarose) (Peng et al., 1990) with the same concentration of imazethapyr and proliferated for another three weeks after which time they were transferred to fresh medium without selection reagent for another three weeks. Resistant calli were transferred to MSKT medium (MS (Murashige and Skoog, 1962) basal medium supplemented with 5 mg/l kinetin, 5 mg/l zeatin, 0.1 mg/l naphthaleneacetic acid, 3% sucrose and 0.6% agarose) for 2–3 weeks for shoot induction. Small shoots were transferred to MSO Medium (MS medium supplemented with 3% sucrose and 0.6% agarose with no plant growth regulators, Peng et al., 1992) for root formation. Two to three weeks later. plantlets were transplanted to a mixture of half soil and half Metromix 360 (The Scotts Company, Marysville, Ohio 43040) in 6 inch pots in the greenhouse. Plants were bagged to assure self-pollination and grown to maturity to produce seeds. In rice, the apparent transformation efficiency based on resistant colonies recovered after selection ranged from 1 to 14 per million protoplasts treated. Three to 10 percent, with one exception, of the selected calli regenerated into plants (Table 1).

Example 3

PCR Analysis of Putative Transgenic Rice Plants

DNA was isolated from individual rice plants using the well known procedure of Wang et al (1993). PCR conditions were as follows: 50 $\mu$l reaction volume containing 1×PCR Buffer (10 mM Tris-HCl, pH 8.3, 50 mM KCl, 1.5 mM MgCl$_2$, 0.1% Triton X-100), 200 mM each deoxynucleoside triphosphate, 1.25 units of AmpliTaq DNA Polymerase (all from Perkins Elmer Applied Biosystems, Foster City, Calif.), and 7.5 pmoles of each primer. The reaction mixture was heated to 95° C. for 1 min, 55° C. for 2 min, 72° C. for 2 min, followed by incubation at 72° C. for 5 min. To identify the maize X112 AHAS gene a forward primer 5'AGCAGGGAGGCGGTGCTTGC-3', (SEQ ID NO:1), and reverse primer 5'AAGGGTCAACATTCCAGCGGT-3', (SEQ ID NO:2), the primers were designed to amplify a 251 bp fragment from the 3' end of the gene. The primers were obtained from Genosys Giotechnologies, Inc., The Woodlands, Tex. 77380-3600. PCR analysis verified the presence of the introduced maize ahas 2 gene in the T0, T1, and all T2 plants derived from a resistant line. In one example, of the 15 T1 plants assayed for the PCR reaction product, 12 and 13 were positive for the transgene in Line 16 and Line 29, respectively, indicating that the transgene was indeed stably transmitted to some of the T1 progeny plants (Table 2). The absence of the transgene from some of the T1 plants was expected due to the hemizygous status of the transgene in the original T0 plants.

Example 4

Germination Tests

T2 seeds harvested from individual T1 plants were sterilized in 50% Clorox® bleach (2.3% sodium hyperchlorite)

for 30 min followed by a thorough rinse with autoclaved water and pre-germinated in water for 2–3 days. Thirty to 35 pre-germinated seeds were transferred to the surface of folded paper towels placed perpendicular to the bottom of a Magenta box (Sigma, St. Louis, Mo.) to which 20 ml of H2O containing 5 µM imazethapyr (AC263,499, tech grade) was added. The seedlings were grown under 12 hr light at 26° C. for about a month. Seedlings that survived the imazethapyr treatment were scored as resistant and those that died as susceptible. 5.0 µM imazethapyr, equivalent to 5 times the threshold, was used for subsequent seed germination tests of the T2 generation. T2 seeds harvested from 16 T1 lines derived from T0 plant No. 26 and those from 15 T1 lines derived from T0 plant No. 29 were screened in the seed germination tests. After 1 month treatment with 5 µM imazethapyr, all control seeds died, and resistant transgenic plants survived and continued to grow with no apparent differences from control plants treated with water. Results from the seed germination tests indicated that there were a total of 10 T1 lines producing all resistant T2 seeds; 5 were all susceptible and 14 of them had T2 seeds segregating as resistant or susceptible to the imazethapyr treatment (Table 2). Statistic analysis of data obtained from the seed germination test indicated that in Lines 26 and 29, the imazethapyr resistant trait conferred by the introduced maize XI12 ahas 2 gene was probably a single dominant trait inherited in a Mendelian fashion (Table 2).

Example 5

In vitro Growth Analysis of Transgenic Rice Cells

Immature embryos (12–14 days after fertilization) were dissected from transgenic homozygous T2 plants, identified as 26-4 in FIG. 1, or seed-grown Nortai plants and placed in N6 basal medium (Chiu et al., Sci. Sin 18:659–68, 1975) supplemented with 2 mg/l 2,4-D, 3% sucrose, 0.6% agarose (3SN6d2) amended with 0, 0.01, 0.033, 0.1, 0.3, 1.0, 3.3, 10, 25, or 50 µM imazethapyr (AC263,499). Five embryos were placed on one 10×60 mm Petri dish with two to three plates for each concentration as replications. Three weeks later, in vitro cellular response was monitored by measuring the fresh weight of callus derived from individual embryos.

Cell suspension cultures were initiated from immature embryo-derived calli from either transgenic homozygous T2 plant 26-4-10 or Nortai plants in 3SN6d2 liquid medium and cultured two to three months prior to treatment with various concentrations of imazethapyr. The suspension cells were filtered through a 40µ nylon mesh, collected, and resuspended in 3SN6d2 liquid medium 0.2 ml of the suspended cells were loaded onto a Millipore filter, then placed on top of agarose solidified medium containing 0, 0.1, 0.25, 0.5, 1.0, 2.5, 5, 10, 25, or 50 µM imazethapyr (AC263,499). Three weeks later, all cultures were transferred once to fresh media with the same concentrations of imazethapyr and grown for another 5 weeks. Fresh weight was measured at the end of an 8-week culture period.

Transgenic and control embryos responded well to callus initiation on media without imazethapyr. When placed on media amended with imazethapyr, callus induction from immature embryos isolated from Nortai plants (control) was totally inhibited at 0.1 µM and growth was reduced to less than 50% at 0.03 µM with response to callus initiation. For transgenic embryos, normal callus induction and growth on media amended with imazethapyr up to 1 µM was observed, with about 50% reduction in growth at 3.3 µM and no callus induction at 10 µM (FIG. 1A). It is, therefore, apparent that the transgenic embryos had a 100-fold increase in resistance to imazethapyr in vitro.

Figure 1B:
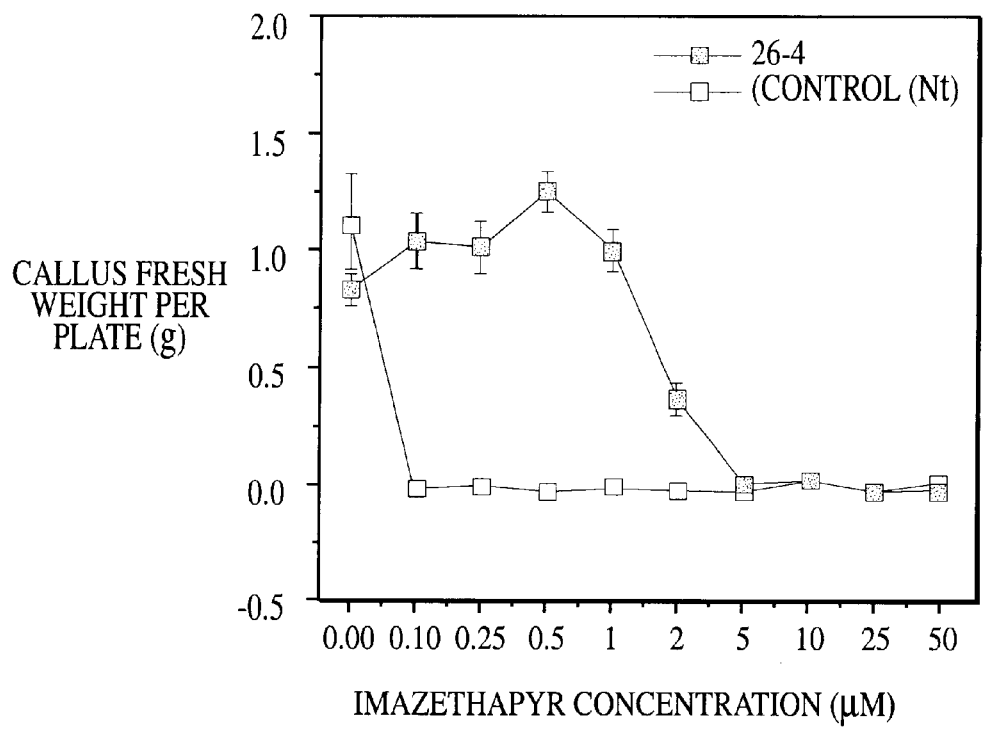

Fast growing suspension cultures with cell clusters less than 40µ in diameter were evaluated for their in vitro response to imazethapyr. In the absence of imazethapyr, there was no visible difference in the growth of transgenic and control cells. In the presence of imazethapyr, the growth of control cells was halted at 0.1 µm, the lowest concentration used in the experiment, and growth of transgenic suspension cells was normal up to 1.0 µm followed by a sharp decrease at 2 µm with no growth at 5 µm (FIG. 1B).

Example 6

AHAS Activity in Transgenic Plants

In vitro AHAS assays were performed to understand the basis of herbicide tolerance in the transgenic plants. Previously published procedure was used for the extraction and in vitro assay for AHAS activity (Singh et al. 1988). The lower portions of the shoots were used as the source of plant tissue for the assay. The desalted crude extracts were used for the in vitro enzyme assays. Acetolactate produced by the enzyme was converted to acetoin, which was measured by the Westerfield assay system (Westerfield 1945). The specific activity of AHAS was about 30% higher in Line 26 (67 nmoles/mg protein/h) and Line 29 (64 nmoles/mg protein/h) compared to the activity in Nortai (Nt) (50 nmoles/mg protein/h). A significant portion of the enzyme activity from the tolerant Line 26 and Line 29 were insensitive to inhibition by imazethapyr and imazapyr (FIG. 2) when compared with the inhibition curve for the normal enzyme from Nortai plants. Interestingly, AHAS activity from all three lines was inhibited in a similar manner by chlorsulfuron (FIG. 2). This result illustrates that the maize XI12 mutant ahas 2 gene is selectively resistant the imidazolinone herbicides only.

Example 7

Greenhouse Performances of Rice Plants Sprayed with PURSUIT® Imazethapyr

We evaluated the response of transgenic rice to PURSUIT® imazethapyr application in the greenhouse. In this experiment, we included 2 transgenic lines and their untransformed counterpart (Nt). The transgenic lines, designated as Line 26 and 29, were T3 progeny derived from previously identified homozygous resistant transgenic plants containing the maize XI12 ahas2 gene driven by its own promoter. All seeds were pre-germinated in water for 2–3 days then grown in a planting mixture consisting of 1:1 soil and MetroMix 360 (The Scotts Company, Marysville, Ohio 43040) in 6-inch pots (2 seeds per pot) in the greenhouse and sprayed with PURSUIT® imazethapyr at 63, 125, or 250 g ai/ha. For post-emergence application, the plants were sprayed 15 days after seeding, at which time most plants had 3 leaves. For pre-emergence treatment, PURSUIT® imazethapyr was sprayed one day after seeding. Each treatment contained 20 plants and, and 3 replicates per treatment. One set of materials was not sprayed and used as control. The plants were grown in the greenhouse and harvested at maturity. The amount of PURSUIT® imazethapyr applied in this study (63, 125, or 250 g ai/ha) was close to 1, 2 or 4× field application rate for imi-resistant corn (refer to Table 3) since PURSUIT® imazethapyr is not currently labeled for use in rice fields. A custom designed belt sprayer was operated as described (Newhouse et al. 1992) for all herbicide applications. Five plants from each treatment were randomly chosen and individually measured for morphological traits. Means and standard deviations were calculated over three replications. Plant heights were measured from the base of the plant to the tip of the flag leaf 93 days after herbicide applications (DAH) and number of tillers per plant were counted 102–103 DAH. Data on number of panicles per plant and yield were collected after plants were harvested.

Results of this experiment, which are summarized in Tables 4 & 5, demonstrate that: (1) In the pre-emergence application, transgenic lines were resistant to all rates of PURSUIT® imazethapyr used. Control (Nortai) plants were completely killed at 125 and 250 g/ha PURSUIT® imazethapyr, and had about 20% reduction in plant height and 40% reduction in yield at 63 g/ha. Transgenic plants of Lines 26 and 29 survived at all rates applied, grew very well, and produced yields comparable to their untreated counterparts (Table 4). (2) In the post-emergence application, transgenic plants again performed well, and comparable yields were obtained from all treatments (Table 5). For the controls, 63 g ai/ha PURSUIT® imazethapyr had some effect, higher rate 125 g ai/ha) caused a dramatic reduction in all the traits measured, and 250 g ai/ha killed all plants (Table 5). (3) In general, without herbicide treatment, untreated transgenic plants were shorter and had more tillers and panicles than untransformed control plants. Untransformed Nortai plants had approximately 10% (in postemergence experiment) to 20% (in preemergence experiment) higher yields than transgenic plants.

Example 8

Response of Transgenic Rice Plants to Application of Various Herbicides

A total of 9 herbicides, 5 imidazolinones, two rice herbicides and ACCENT® (nicosulfuron) and CLASSIC® (clorimuron-ethyl) were applied in this study. Materials and methods were basically the same as described above, except that instead of 6" pots, flats with 18 (3"×3" per cell) cells were used, and 10–12 seeds were planted to one 3"×3" cell. Ten plants were maintained in one cell in the post-emergence application. Each herbicide was sprayed at 4 different rates, 1, 2, 4, and 6×, as either pre or post-emergence applications with three replications per treatment. The name and amount of herbicide applied in this experiment and information relevant to their commercial applications are listed in Table 3. For simplicity and convenience, the lowest concentration used is referred as 1× rate, 2, 4 and 6× rates can be calculated as multiples of 1×.

To monitor plant response to various herbicides, data on fresh weight was collected. For pre-emergence applications, all plants from one cell were harvested 32 days after spraying (36-day old plants) and weighed. Twenty-nine days after herbicide application, 5 plants (44-day old plants) from each cell in the post-emergence application, were cut and weighed individually. Mean fresh weight for each treatment was calculated over three replications. The remaining 5 plants were grown in the greenhouse to maturity at which time, panicles of 3 plants were collected, and number of filled seeds and number of total kernels were counted to determine percentage of seed set.

The results from visual observation and from fresh weight measurements show that overall, transgenic plants performed better in post-emergence applications than they did in pre-emergence applications, and the two rice herbicides (AC322,140 cyclosufamuron and LONDAX® bensulfuron-methyl) had a minimal effect on growth of all plants treated. In post-emergence applications, growth of transgenic plants was not affected by any of the imidazolinone herbicides—CADRE® imazameth, ARSENAL® imazapyr, PURSUIT® imazethapyr, RAPTOR® imazamox and SCEPTER® imazaquin up to 4× and was slightly affected at 6×. ACCENT® nicosulfan and CLASSIC® clorimuron-ethyl greatly affected plant growth even at 1× rates. A similar trend was observed in the pre-emergence applications, except that growth of both transgenic lines was affected by application of 2× or higher SCEPTER® imazaquin and 6×RAPTOR® imazamox. Low rates of ACCENT® nicosulfan (1 and 2×) did not affect plant fresh weight of two transgenic and control plants greatly. Data presented in Table 6 demonstrates that: on average, plants without herbicide treatments and plants treated with two rice herbicides (AC322,140 cyclosufamuron and LONDAX bensulfuron-methyl) had 80–98% seed-set. Control (NT) plants treated with imidazolinone herbicides at most rates (except 1×PURSUIT® imazethapyr, 1 and 2×CADRE®), ACCENT® at all rates, and CLASSIC® clorimuron-ethyl at 4 and 6× died without producing seed. PURSUIT® imazethapyr, RAPTOR® imazamox, CADRE® imazameth, SCEPTER® imazaquin (at all rates tested) and low rates of ARSENAL® imazapyr (1 to 2×) had no influence on seed set (percentage of filled seeds over total number of kernels per panicle) and total number of kernels per panicle in two transonic lines. An average of about 85% seed set was obtained from these treatments. However, with applications of 4× (96 g ai/ha) and 6× (144 g ai/ha) ARSENAL® imazapyr, seed set dropped to 20% or lower in the two transgenic lines even though growth of these plants as reflected by fresh weight, and total number of kernels per panicle was not dramatically affected (FIG. 3 and Table 6). ACCENT® nicosulfan and CLASSIC® clorimuron-ethyl affected both seed set and total number of kernels per panicle in transgenic plants.

Example 9

Corn Transformation and Selection

Dissect Immature Embryos

Depending on the size of immature embryos, collect ears at 9–12 days after pollination. Seed (HiIIA and A188) was obtained from USDA/ARS and Crop Sciences, UIUC, Urbana, Ill. 61801-4798. Spray 70% ethanol and 10% Lysol several times from outer to inner husks to surface sterilize the cob. Remove all the husks, cut off silks with a scalpel, and shave the top of the kernel. Immature embryos ranging from 0.8 to 1.2 mm in size were isolated under a dissecting microscope and placed into a 2.5 ml tube containing the LS-inf medium (all media for corn and wheat transformation are adapted from Ishida et al., 1996). About 100 embryos for each tube are appropriate. Vortex the immature embryos in solution gently and remove the liquid solution. Wash the immature embryos one more time in the same manner with the LS-inf medium.

Co-cultivation

Add 1 ml Agrobacterium cells harboring the maize X112 mutant ahas 2 gene to the tube containing the immature embryos and gently vortex the mixture for 30 sec followed by 5 minute incubation at room temperature. Transfer the immature embryos to a Petri-dish and gently plate the immature embryos with scutellum side up and away from the medium onto LSD1.5 medium supplemented with 100–200 $\mu$M AS (acetosyringeone). Up to two hundred embryos can be plated to one plate. Seal plates with Parafilm film for three days followed by porous tape (3M, St Paul Minn. 55144) until the end of the co-cultivation stage. Incubate the immature embryos at 26° C. in the dark for 7 days. Three to four days co-cultivation was recommended by Japan Tobacco, Inc. (see Ishida et al., 1996) but 7 days was needed in our hands.

1st Selection

After 7 days of co-cultivation, carefully transfer the immature embryos to fresh LSD1.5 medium supplemented with 250 mg/l cefotaxime and 0.05 μM imazethapyr (AC 263,499) in a 100×25 mm Petri-dish. Usually 25 embryos are plated on one plate. Seal the plates with vegetable tape. Grow the immature embryos at 26° C. in the dark for 2 to 3 weeks.

2nd Selection

Looking through a dissecting microscope and using a pair of forceps pick callus cells that are actively growing and transfer to fresh medium amended with 250 mg/l cefotaxime and 0.5 μM imazethapyr. Seal the plates with produce tape (purchased from Winans McShane, Benardsville, N.J. 07924). Grow the material at 26° C. in the dark for 3 weeks.

3rd Selection

Repeat the above selection processes and grow the material for another two to three weeks under the same conditions.

Plant Regeneration

For shoot induction, select callus materials that are actively growing under a dissecting microscope and transfer to LSZT5 medium (the same as LSZ in Yoshida et al.,1996), supplemented with 0.25 μM imazethapyr. Grow the callus materials at 14/10 hr light/dark and 26/24° C. for two to three weeks or until visible shoot formation. Transfer the plantlets to a Magenta box containing MS4RG (MS medium supplemented with 3% sucrose, 0.8% agar and without plant regulator and imazethapyr) for root formation. Transplant the plantlets with roots to pot with MetroMix 360 (The Scotts Company, Marysville, Ohio 43040) in a 15-cell flat and grow the plants in the greenhouse.

Spray Regenerated Plants

Ten to 14 days after transplanting (when the plants reach 3–4 leaf stage), spray the regenerated plants with 2× or 4×PURSUIT® imazethapyr (1×=62.5 g/ha). Two to three weeks later, take score of the experiment and transfer the surviving plants to a one-gallon pot and grow plants to flowering. Self- or cross-pollinate transgenic plants as desired. About 45 days after pollination harvest the seed. Dry seed and store properly.

Evaluation of Transgenic Progeny

Grow one corn plant per pot (5×5 inch) in a 3×5 flat till three- to four-leaf stage (about 9 to 13 days depending on the weather). On the day of spraying, water the plants well and let excess water drip out. Spray plants on a belt-sprayer with the imidazolinone herbicides at desired rates. Do not top water plants for three days if weather permits. When temperature was too high, base water plants to prevent wilting. Closely observe the plants for the next two to three weeks. Symptoms of herbicide injury will be visible three days after spraying and susceptible plants will die within two to three weeks depending on temperature.

The plants were rated on a scale of 0–5 with 0 for dead plants and 5 for healthy plants with no or minimum injury.

The transformation efficiency of corn, calculated as percent of immature embryos produced at least one imidazolinone-resistant transgenic plant averaging about 2% and reaching as high as 16%–20% in some experiments (Table 7).

Transgenic corn plants were evaluated in the greenhouse for resistant levels to various imidazolinone herbicides and inheritance of the transgene. For corn, our protocol involved self- or cross-pollinating the transgenic plants for 2 to 3 generations and spraying T1 progeny plants to identify the resistant vs. susceptible plants. Detailed analysis for levels of herbicide susceptance and the inheritance pattern. Identification of lines homozygous for the transgene is carried out in T2 generation with self-pollination and cross-pollination derived progeny plants. For example, transgenic plant 1B1 (genotype A188) which survived initial spray treatment and showed positive in PCR reaction was self-pollinated and cross-pollinated with B73 to produce T1 seed which were again self- or cross pollinated to produce T2 seed (FIG. 5). B73 and Mo17 lines were obtained USDA/ARS and Crop Sciences, UIUC, Urbana, Ill. 61801-4798. T1 plants were treated with 4×PURSUIT® imazethapyr (250 ai g/ha) at 3-leaf stage and rated as either resistant or susceptible to the herbicide. A total of 6 self and 8 B73×1B1 T1 plants were sprayed and all survived the herbicide treatments.

Two transgenic hybrids BAa-4 and MAa-7 lines (see FIG. 5 for their pedigree), a non-transformed control line B×A (B73×A188), 8962IT (heterozygous XI12 imi-tolerant corn line), 8962 (wild type control) and 3395IR (homozygous XA17 imi-resistant corn line) (8962IT and 8962 were from ICI, now Garst Seed Company, Slater, Iowa 50244, and 3395IR was from Pioneer Hi-Bred International Inc, Iowa 50306-3453). Plants were sprayed with 4, 8, 16 or 20×PURSUIT® imazethapyr, ARSENAL® imazapyr, CADRE® imazameth or RAPTOR® imazamox. Plants were scored 0 to 5 (with 0 being dead plants, 5 being healthy plants with no injury) individually 16 days after herbicide treatments. Table 8 lists the lines and herbicide rates used and summarizes the results of this experiment. Our observation indicated that both transgenic lines showed no injury up to 16×ARSENAL® imazapyr (384 g/ha), 8×PURSUIT® imazethapyr (500 g/ha), 4×CADRE® imazameth (800 g/ha) while all control plants were dead at 4×of any tested herbicides (FIG. 5). At 4×RAPTOR® imazamox (160 g/ha), one transgenic line (MAa-7) also performed well, while growth of the other transgenic line (BAa-4) was slightly affected. For the four tested imidazolinones, transgenic plants could tolerate higher rates of ARSENAL® imazapyr, PURSUIT® imazethapyr, than CADRE® imazameth and RAPTOR® imazamox.

Example 10

Wheat Transformation and Selection

Sterilization and Dissecting Immature Embryos

Durum wheat, varieties Ciccio and Colosseo obtained from Eurogen S. r. l (C. da Grottacalda, Strada Turistica, Bivio Ramata, Grottacalda km 4,500, 94015 Piazza Amerina (EN), Italy) were used for transformation. Once wheat plants start anthesis, mark each head with a small piece of tape with the date of first flowering on it. Depending on the size of immature embryos (range from 0.5 to 1.0 mm), collect wheat spikes 12 to 16 days after anthesis. Separate kernels from branches and place 100–200 kernels in a 25×100 mm Petri-dish. The kernels were sterilized and immature embryos were dissected with a scalpel under a microscope. About 100–200 embryos were placed in a micro-centrifuge tube containing 2 ml LS-inf medium and vortexed gently. The immature embryos were washed twice with LS-inf medium.

Co-cultivation

Add 1 ml bacteria cells to the tube containing the immature embryos and vortex gently for 30 sec. The immature embryos were incubated in the bacterial solution for 5 min at room temperature. After incubation, the immature embryos were plated to a Petri-dish containing LSD1.5 medium supplemented with 100 μM AS with scutellum side up and away from the medium. The plates were sealed with Para-film for three days followed by porous tape for 4 days. Total incubation time for co-cultivation was 7 days.

1st Selection

After co-cultivation, carefully transfer the immature embryos to fresh LSD1.5 medium supplemented with 250 mg/l cefotaxime and 0.1 µM imazamox (AC299,263) in a 100×25 mm Petri-dish. If there is formation of embryonic shoots at this stage, cut off the shoots from the embryo before transferring. Plate 25 embryos per plate. Seal plates with vegetable tape. Grow the immature embryos at 14/10 day/night with 26° C./24° C. temperature for 2 weeks.

2nd Selection

Pick up actively growing callus cells with a pair of forceps under a dissecting microscope and transfer to fresh medium amended with 250 mg/l cefotaxime and 0.3 µM imazamox (AC299,263). Grow the culture under the same conditions specified above for two weeks.

3rd Selection

Repeat the above selection processes and grow the materials for two week.

Plant Regeneration

Usually, there is small shoot formation already at this stage. Carefully transfer callus pieces with shoots on the surface to LSZT5 medium supplemented with 0.1 µM AC299,263. Grow the immature embryos at 14/10 day/night with 26° C./24° C. temperature for 2 to 3 weeks. Transfer the shoots to Magenta box containing medium for root induction. Transplant the plantlets to pot mix in a 15-cell flat and grow the plants in the greenhouse.

Spray Regenerated Plants

About two weeks after transplanting when the plantlets reach 3- to 4-leaf stage, spray the regenerated plants with 25 mg/ha RAPTOR® imazamox. Three weeks later transplant survival plants to one-gallon pots and grow the plants to flowering. When the plants start to flowering, cover each head with a pollination-bag to ensure self-pollination. Allow plants to grow to maturity. Harvest, dry and store seed properly.

Evaluation of Transgenic Progeny

Sow seed to 3×5-cell flats at about 10 seed per cell. Grow the plants for about two weeks. On the day of spraying, water plants well and let excess water drip out. Spray plants on a belt-sprayer with the imidazolinone herbicides at desired rates. Do not water plants for three days. Resume regular water schedule three days after spraying. Closely observe the plants for the next two to four weeks. Symptoms of herbicide injury will be visible two weeks after spraying and susceptible plants will die four to six weeks later. We usually measure plant height and score the plant morphology with a 0 to 10 rating with 0 for dead plants and 10 for healthy plants with no or minimum injury.

Wheat transformation efficiency, calculated as percent of immature embryos produced at least one imidazolinone-resistant transgenic plant ranged from 0.4 to 3.1% (Table 7). A fertile regenerant 0407-1 generated from early transformation experiment with Agrobacterium (LBA4404) containing pAC1558 was evaluated for resistance to RAPTOR® imazamox post emergence. Untransformed Ciccio and Closseo plants were very sensitive to RAPTOR® imazamox and dead at very low rate. Transgenic wheat plants showed resistance to RAPTOR® imazamox over non-transformed control (FIG. 6B).

This rate (50 g/ha) caused death in non-transformed Ciccio (FIG. 6). Out of the 288 T1 transgenic plants, 70 survived and 218 dead after the herbicide spray, making the ratio between resistant and sensitive plants close to 1:3. The resistant plants survived the herbicide treatment, but displayed increased tillers and 33–70% stunting in addition to delayed plant development. PCR analysis of the plant sample revealed a complete insert of the trasngene indicating that the 0407-10 plant and its progeny were transformed with the maize mutant XI112 ahas gene conferring resistant AHAS enzyme against the imidazolinone herbicides.

We also analyzed T2 progeny plants from one of the best lines of 0407-1-10. T2 seeds were planted at 10 seeds per pot and two pots per line were sprayed at 0, 10, 20, 30, 40 and 50 g/ha RAPTOR® imazamox. Most plants did show an increase in resistance over non-transformed control (FIG. 6B). For example, plant height of the resistant transgenic plants was reduced by about 25% at 20 g/ha while non-transformed plants were completely killed at rate above 10 g/ha.

While the preferred embodiment of the invention has been illustrated and described, it will be appreciated that various changes can be made theein without departing from the spirit and scope of the invention.

TABLE 1

Transformation and plant regeneration efficiencies of rice protoplasts transformed with the maize mutant ahas2 gene and selected on medium amended with 0.5 µM imazethapyr.

| Expt. No | Transform No. | Protoplasts used × 10⁻⁶ | No. Res. calli recovered | No. transformants per 10⁶ protoplasts | No. plants regenerated |
|---|---|---|---|---|---|
| 1 | 1 | 25 | 26 | 1 | 0 |
| 1 | 2 | 25 | 110 | 4.4 | 3 |
| 2 | 1 | 7.5 | 31 | 4.1 | 1 |
| 2 | 2 | 7.5 | 96 | 12.8 | 11 |
| 2 | 3 | 7.5 | 71 | 9.5 | 8 |
| 2 | 4 | 7.5 | 101 | 13.5 | 10 |
| 3 | 1 | 20 | 85 | 2.1 | 9 |

TABLE 2

Results of PCR analysis of T1 plants and inheritance patterns of the imidazolinone resistant trait in transgenic rice plants.

| T0 No. | T1 PCR+/− ratio | T2 progeny response to imazathepyr | $\chi^2$ ratio* |
|---|---|---|---|
| 26 | 12/3 | 5 lines all resistant<br>8 lines segregating (179R:49S)<br>3 lines all susceptible | 1.31 n.s.* |
| 29 | 13/2 | 5 lines all resistant<br>6 lines segregating (157R:40S)<br>2 lines all susceptible | 2.07 n.s. | n.s.*the observed segregation ratio is not significantly different from expected 3:1 ratio at the 0.05 probability level when tested by $\chi^2$ distribution.

TABLE 3

Summary on herbicides and amount applied for testing transgenic rice plants, and their commercial applications.

| Commercial name or AC No. | Chemical name of active ingredient | Amount used as 1× rate (g ai/ha) | Field application major crop, method, rate (g ai/ha) |
|---|---|---|---|
| PURSUIT ® | imazethapyr | 62.5 | Soybean, Post, 53–70; Imi-corn, Post, 70 |
| CADRE ® | imazameth | 32 | Peanut, Post, 70 |
| ARSENAL ® | imazapyr | 24 | Non-crop, Post, 560–1700 |
| RAPTOR ® | imazamox | 32 | Soybean, Post, 35–45 |
| SCEPTER ® | imazaquin | 125 | Soybean, Post, 70–140; Pre, 105–140 |
| ACCENT ® | nicosulfuron | 35 | Corn, Post, 70 |
| CLASSIC ® | chlorimuron-ethyl | 5 | Soybean, Post, 8.8–13 |
| AC322, 140 | cyclosulfamuron | 20 | Rice, Pre, 25–40 |
| LONDAX ® | bensulfuron-methyl | 68 | Rice, Pre/Post, 42–70 |

TABLE 4

Summary of morphological characteristics of rice measured for pre-emergence treatment

| PURSUIT ® imazethapyr | | Plant height (cm) | | No. tillers/ plant | | No. panicles/ plant | | Yield (g/5 plants) | | |
|---|---|---|---|---|---|---|---|---|---|---|
| Line | g/ha | Mean | Sdv | Mean | Sdv | Mean | Sdv | Mean | Sdv | % 0× |
| 29 | 0 | 93.5 | 4.2 | 18.1 | 1.8 | 17.9 | 1.3 | 168.3 | 5.5 | 100 |
|  | 63 | 92.7 | 3.2 | 16.2 | 1.1 | 15.6 | 1.2 | 156.3 | 5.7 | 93 |
|  | 125 | 95.1 | 5.1 | 14.3 | 2.6 | 16.3 | 1.5 | 166.7 | 12.4 | 99 |
|  | 250 | 93.1 | 1.9 | 16.3 | 2.0 | 16.2 | 1.1 | 155.3 | 2.5 | 92 |
| 26 | 0 | 91.1 | 8.1 | 14.8 | 2.0 | 14.6 | 1.8 | 153.3 | 44.4 | 100 |
|  | 63 | 92.2 | 4.4 | 14.3 | 1.7 | 13.2 | 0.5 | 155.3 | 2.1 | 101 |
|  | 125 | 89.7 | 4.2 | 15.3 | 2.8 | 14.4 | 2.1 | 170.0 | 26.5 | 111 |
|  | 250 | 88.5 | 3.3 | 13.3 | 0.9 | 15.7 | 0.4 | 167.0 | 6.9 | 109 |
| Nt | 0 | 111.8 | 3.4 | 11.3 | 1.0 | 10.1 | 0.3 | 197.3 | 10.8 | 100 |
|  | 63 | 98.0 | 1.1 | 6.5 | 6.1 | 5.7 | 4.9 | 110.7 | 16.2 | 56 |
|  | 125 | 0 | 0 | 0 | 0 | 0 | 0 | 0 | 0 | 0 |
|  | 250 | 0 | 0 | 0 | 0 | 0 | 0 | 0 | 0 | 0 |

TABLE 5

Summary of morphological characteristics of rice measured for post-emergence treatments

| PURSUIT ® imazethapyr | | Plant height (cm) | | No. tillers/ plant | | No. panicles/ plant | | Yield (g/5 plants) | | |
|---|---|---|---|---|---|---|---|---|---|---|
| Line | Rate | Mean | Sdv | Mean | Sdv | Mean | Sdv | Mean | Sdv | % 0× |
| 29 | 0 | 113.5 | 1.1 | 30.7 | 8.4 | 27.5 | 8.3 | 213.3 | 33.5 | 100 |
|  | 63 | 112.5 | 3.3 | 34.5 | 5.7 | 27.7 | 6.6 | 199.0 | 59.4 | 93 |
|  | 125 | 114.1 | 3.0 | 28.3 | 1.0 | 24.5 | 4.8 | 240.7 | 45.2 | 113 |
|  | 250 | 110.2 | 3.9 | 24.1 | 1.6 | 23.0 | 7.0 | 197.3 | 43.5 | 93 |
| 26 | 0 | 109.6 | 6.8 | 31.7 | 0.9 | 26.2 | 3.8 | 210.7 | 23.0 | 100 |
|  | 63 | 110.1 | 6.0 | 27.1 | 4.6 | 25.3 | 6.0 | 206.7 | 38.2 | 98 |
|  | 125 | 108.1 | 1.4 | 25.6 | 6.2 | 22.8 | 6.2 | 206.0 | 34.6 | 98 |
|  | 250 | 110.3 | 2.2 | 25.4 | 4.7 | 21.7 | 4.5 | 202.7 | 50.6 | 96 |
| Nt | 0 | 127.8 | 4.9 | 20.0 | 4.3 | 20.5 | 3.8 | 229.0 | 33.5 | 100 |
|  | 63 | 117.3 | 6.5 | 20.0 | 4.0 | 15.7 | 1.7 | 227.0 | 68.9 | 99 |
|  | 125 | 94.5 | 10.3 | 13.5 | 1.6 | 13.9 | 3.6 | 120.0 | 58.5 | 52 |
|  | 250 | 0 | 0 | 0 | 0 | 0 | 0 | 0 | 0 | 0 |

TABLE 6

Summary of yield data for non-transgenic and transgenic rice lines

| Line | Herbicide | No. filled seeds/ 3 panicles | | | | | Total No. of kernels/ 3 panicles | | | | | % seed-set | | | | |
|---|---|---|---|---|---|---|---|---|---|---|---|---|---|---|---|---|
| | | 0× | 1× | 2× | 4× | 6× | 0× | 1× | 2× | 4× | 6× | 0× | 1× | 2× | 4× | 6× |
| Nt | None | 154 | — | — | — | — | 163 | — | — | — | — | 95 | — | — | — | — |
| | PURSUIT ® | — | 38 | 0 | 19 | 0 | — | 47 | 0 | 21 | 0 | — | 35 | 0 | 10 | 0 |
| | CADRE ® | — | 92 | 76 | 0 | 0 | — | 94 | 82 | 0 | 0 | — | 98 | 83 | 0 | 0 |
| | ARSENAL ® | — | 0 | 0 | 0 | 0 | — | 0 | 0 | 0 | 0 | — | 0 | 0 | 0 | 0 |
| | RAPTOR ® | — | 0 | 0 | 0 | 0 | — | 0 | 0 | 0 | 0 | — | 0 | 0 | 0 | 0 |
| | SCEPTER ® | — | 0 | 0 | 0 | 0 | — | 0 | 0 | 0 | 0 | — | 0 | 0 | 0 | 0 |
| | ACCENT ® | — | 6 | 0 | 0 | 0 | — | 24 | 0 | 0 | 0 | — | 3 | 0 | 0 | 0 |
| | CLASSIC ® | — | 87 | 90 | 0 | 0 | — | 99 | 97 | 0 | 0 | — | 87 | 92 | 0 | 0 |
| | AC 322,140 | — | 175 | 158 | 83 | 118 | — | 187 | 171 | 86 | 121 | — | 93 | 93 | 95 | 98 |
| | LONDAX ® | — | 147 | 142 | 113 | 109 | — | 172 | 154 | 127 | 114 | — | 85 | 93 | 91 | 96 |
| 26 | None | 133 | — | — | — | — | 142 | — | — | — | — | 94 | — | — | — | — |
| | PURSUIT ® | — | 143 | 133 | 152 | 107 | — | 157 | 155 | 172 | 138 | — | 91 | 86 | 89 | 77 |
| | CADRE ® | — | 133 | 153 | 124 | 131 | — | 159 | 161 | 143 | 169 | — | 84 | 95 | 87 | 77 |
| | ARSENAL ® | — | 156 | 132 | 10 | 2 | — | 183 | 170 | 170 | 178 | — | 85 | 77 | 6 | 1 |
| | RAPTOR ® | — | 156 | 172 | 166 | 136 | — | 180 | 193 | 183 | 167 | — | 87 | 89 | 91 | 77 |
| | SCEPTER ® | — | 148 | 87 | 147 | 86 | — | 172 | 135 | 166 | 109 | — | 86 | 64 | 88 | 62 |
| | ACCENT ® | — | 82 | 0 | 0 | 0 | — | 145 | 0 | 0 | 0 | — | 34 | 0 | 0 | 0 |
| | CLASSIC ® | — | 95 | 100 | 26 | 10 | — | 114 | 108 | 65 | 18 | — | 83 | 93 | 28 | 20 |
| | AC 322,140 | — | 144 | 158 | 166 | 134 | — | 160 | 168 | 182 | 158 | — | 90 | 94 | 91 | 85 |
| | LONDAX ® | — | 140 | 140 | 102 | 127 | — | 173 | 156 | 136 | 143 | — | 80 | 90 | 65 | 89 |
| 29 | None | 138 | — | — | — | — | 160 | — | — | — | — | 86 | — | — | — | — |
| | PURSUIT ® | — | 125 | 136 | 138 | 141 | — | 146 | 155 | 156 | 160 | — | 85 | 88 | 88 | 87 |
| | CADRE ® | — | 154 | 143 | 126 | 127 | — | 175 | 166 | 154 | 159 | — | 88 | 86 | 82 | 80 |
| | ARSENAL ® | — | 122 | 116 | 41 | 27 | — | 137 | 144 | 179 | 140 | — | 90 | 81 | 26 | 19 |
| | RAPTOR ® | — | 161 | 137 | 152 | 125 | — | 180 | 171 | 167 | 149 | — | 89 | 80 | 91 | 80 |
| | SCEPTER ® | — | 138 | 143 | 131 | 139 | — | 159 | 165 | 155 | 159 | — | 87 | 86 | 85 | 88 |
| | ACCENT ® | — | 94 | 24 | 0 | 0 | — | 114 | 48 | 0 | 0 | — | 82 | 10 | 0 | 0 |
| | CLASSIC ® | — | 115 | 112 | 35 | 5 | — | 130 | 132 | 45 | 14 | — | 88 | 85 | 37 | 4 |
| | AC 322,140 | — | 150 | 172 | 129 | 134 | — | 166 | 187 | 160 | 154 | — | 91 | 92 | 80 | 87 |
| | LONDAX ® | — | 125 | 133 | 155 | 150 | — | 156 | 148 | 177 | 175 | — | 80 | 90 | 87 | 86 |

TABLE 7

Transformation efficiency of corn and wheat

| Expt. # | Species | Genotype | # IE | Constructs | # IE regenerated plants | # resistant plants | TE/Trt % |
|---|---|---|---|---|---|---|---|
| 1 | Maize | AxHiIIA F2 | 100 | pAC1558/L | 3 | 2 | 3.0 |
| 2 | Maize | AxHiIIA F1 | 80 | PAC1558/L | 13 | 34 | 16.3 |
| 3 | Maize | A188 | 100 | PAC1558/L | 2 | 2 | 2.0 |
| 4 | Maize | AxHiIIA F2 | 48 | PAC1558/L | 2 | 19 | 4.2 |
| 5 | Maize | AxHiIIA F2 | 102 | PAC1558/L | 3 | 9 | 2.9 |
| 6 | Wheat | Ciccio | 180 | PAC1558/L | 2 | 2 | 1.1 |
| 7 | Wheat | Ciccio | 200 | PAC1558/L | 1 | 1 | 0.5 |
| 8 | Wheat | Ciccio | 250 | PAC1558/L | 1 | 1 | 0.4 |
| 9 | Wheat | Ciccio | 220 | PAC1558/L | 2 | 2 | 0.9 |
| 10 | Wheat | Ciccio | 124 | PAC1558/L | 4 | 4 | 3.1 |

TABLE 8

Performance of transgenic corn lines treated with various herbicides

| Treatment | Line | Score | | | | | M.S. |
|---|---|---|---|---|---|---|---|
| Control | BxA | 5 | 5 | 5 | 5 | 5 | 5 |
| | BAa-4 | 5 | 5 | 5 | 5 | 5 | 5 |
| | MAa-7 | 5 | 5 | 5 | 5 | 5 | 5 |
| | 8692 | 5 | 5 | 5 | 5 | 5 | 5 |
| | 8692IT | 5 | 5 | 5 | 5 | 5 | 5 |
| | 3395IR | 5 | 5 | 5 | 5 | 5 | 5 |
| 4× PURSUIT ® imazethapyr 250 g/ha | BxA | 0 | 0 | 0 | 0 | 0 | 0 |
| | BAa-4 | 5 | 5 | 5 | 5 | 5 | 5 |
| | MAa-7 | 5 | 5 | 5 | 5 | 5 | 5 |
| | 8692 | 2 | 2 | 1 | 1 | 2 | 1.6 |
| | 8692IT | 5 | 5 | 5 | 5 | 5 | 5 |
| | 3395IR | 5 | 5 | 5 | 5 | 5 | 5 |

TABLE 8-continued

Performance of transgenic corn lines treated with various herbicides

| Treatment | Line | Score | | | | | M.S. |
|---|---|---|---|---|---|---|---|
| 8× PURSUIT ® imazethapyr 500 g/ha | BxA | 0 | 0 | 0 | 0 | 0 | 0 |
| | BAa-4 | 5 | 5 | 5 | 5 | 5 | 5 |
| | MAa-7 | 5 | 5 | 5 | 5 | 5 | 5 |
| | 8692 | 0 | 0 | 0 | 0 | 0 | 0 |
| | 8692IT | 5 | 5 | 5 | 5 | 4 | 4.8 |
| | 3395IR | 5 | 5 | 5 | 5 | 5 | 5 |
| 20× PURSUIT ® imazethapyr 1.25 kg/ha | BxA | 0 | 0 | 0 | 0 | 0 | 0 |
| | BAa-4 | 4 | 3 | 2 | 4 | 4 | 3.4 |
| | MAa-7 | 0 | 3 | 2 | 4 | 2 | 2.2 |
| | 8692 | 0 | 0 | 0 | 0 | 0 | 0 |
| | 8692IT | 4 | 3 | 4 | 4 | 4 | 3.8 |
| | 3395IR | 5 | 5 | 5 | 5 | 5 | 5 |
| 4× RAPTOR ® imazamox 160 g/ha | BxA | 0 | 0 | 0 | 0 | 0 | 0 |
| | BAa-4 | 3 | 4 | 4 | 4 | 4 | 3.8 |
| | MAa-7 | 4 | 5 | 5 | 5 | 5 | 4.8 |
| | 8692 | 0 | 0 | 0 | 0 | 0 | 0 |
| | 8692IT | 4 | 3 | 2 | 3 | 3 | 3 |
| | 3395IR | 5 | 5 | 5 | 5 | 5 | 5 |
| 8× RAPTOR ® imazamox 320 g/ha | BxA | 0 | 0 | 0 | 0 | 0 | 0 |
| | BAa-4 | 4 | 4 | 0 | 4 | 4 | 3.2 |
| | MAa-7 | 3 | 2 | 3 | 4 | 3 | 3 |
| | 8692 | 0 | 0 | 0 | 0 | 0 | 0 |
| | 8692IT | 3 | 3 | 2 | 2 | / | 2.5 |
| | 3395IR | 5 | 5 | 5 | 5 | 5 | 5 |
| 16× RAPTOR ® imazamox 640 g/ha | BxA | 0 | 0 | 0 | 0 | 0 | 0 |
| | BAa-4 | 3 | 0 | 0 | 1 | 0 | 0.8 |
| | MAa-7 | 1 | 1 | 1 | 1 | 1 | 1 |
| | 8692 | 0 | 0 | 0 | 0 | 0 | 0 |
| | 8692IT | 2 | 1 | 0 | 2 | 0 | 1 |
| | 3395IR | 5 | 5 | 5 | 5 | 5 | 5 |
| 4× ARSENAL ® imazapyr 96 g/ha | BxA | 0 | 0 | 0 | 0 | 0 | 0 |
| | BAa-4 | 5 | 5 | 5 | 5 | 5 | 5 |
| | MAa-7 | 5 | 5 | 5 | 5 | 5 | 5 |
| | 8692 | 0 | 0 | 0 | 0 | 0 | 0 |
| | 8692IT | 4 | 4 | 4 | 4 | 4 | 4 |
| | 3395IR | 5 | 5 | 5 | 5 | 5 | 5 |
| 8× ARSENAL ® imazapyr 192 g/ha | BxA | 0 | 0 | 0 | 0 | 0 | 0 |
| | BAa-4 | 5 | 5 | 5 | 5 | 5 | 5 |
| | MAa-7 | 5 | 5 | 5 | 5 | 5 | 5 |
| | 8692 | 0 | 0 | 0 | 0 | 0 | 0 |
| | 8692IT | 4 | 4 | 3 | 3 | 3 | 3.4 |
| | 3395IR | 5 | 5 | 5 | 5 | 5 | 5 |
| 16× ARSENAL ® imazapyr 384 g/ha | BxA | 0 | 0 | 0 | 0 | 0 | 0 |
| | BAa-4 | 5 | 4 | 5 | 4 | 4 | 4.4 |
| | MAa-7 | 5 | 5 | 4 | 5 | 5 | 4.8 |
| | 8692 | 0 | 0 | 0 | 0 | 0 | 0 |
| | 8692IT | 4 | 3 | 3 | 3 | 3 | 3.2 |
| | 3395IR | 4 | 5 | 5 | 5 | 5 | 4.8 |
| 4× CADRE ® imazameth 400 g/ha | BxA | 0 | 0 | 0 | 0 | 0 | 0 |
| | BAa-4 | 5 | 5 | 5 | 5 | 5 | 5 |
| | MAa-7 | 5 | 5 | 4 | 5 | 5 | 4.8 |
| | 8692 | 0 | 0 | 0 | 0 | 0 | 0 |
| | 8692IT | 4 | 4 | 5 | 5 | 4 | 4.4 |
| | 3395IR | 5 | 5 | 5 | 5 | 5 | 5 |
| 8× CADRE ® imazameth 800 g/ha | BxA | 0 | 0 | 0 | 0 | 0 | 0 |
| | BAa-4 | 3 | 3 | 2 | 2 | 2 | 2.4 |
| | MAa-7 | 2 | 2 | 4 | 4 | 3 | 3 |
| | 8692 | 0 | 0 | 0 | 0 | 0 | 0 |
| | 8692IT | 3 | 2 | 3 | 2 | 3 | 2.6 |
| | 3395IR | 5 | 5 | 5 | 5 | 5 | 5 |
| 16× CADRE ® imazameth 1.6 kg/ha | BxA | 0 | 0 | 0 | 0 | 0 | 0 |
| | BAa-4 | 3 | 1 | 0 | 0 | 0 | 0.8 |
| | MAa-7 | 0 | 0 | 1 | 1 | 1 | 0.6 |
| | 8692 | 0 | 0 | 0 | 0 | 0 | 0 |
| | 8692IT | 1 | 2 | 1 | 2 | 2 | 1.6 |
| | 3395IR | 4 | 4 | 5 | 5 | 5 | 4.6 |

References Cited

Anderson P A, Georgeson M (1989) Herbicide-tolerant mutants of corn. Genome 31: 994–999

Aldemita R R, Hodges T K (1996) *Agrobacterium itumefaciens*-mediated transformation of *japonica* and *indica* rice varieties. Planta 199: 612–617

Barett M (1989) Protection of grass crops from sulfonylurea and imidazolinone toxicity. In Hatzios K K, Hoagniand R E, (eds) Crop safeners for herbicides. Academic Press, New York, pp 195–220

Brown M A, Chiu T Y, Miller P (1987) Hydrolytic activation versus oxidative degradation of Assert herbicide, an imidazolinone aryl-carboxylate, in susceptible wild oat versus tolerant corn and wheat. Pestic Biochm Physiol 27: 24–29

Chaleff R S, Mauvais C J (1984) Acetolactate synthase is the site of action of two sulfonylurea herbicides in higher plants. Science 224:1443–1445

Chaleff R S, Ray T B (1984) Herbicide-resistant mutants from tobacco cell cultures. Science 223: 1148–1151

Chan M T, Lee T M, Chang H H (1992) Transformation of Indica rice (*Oryza saliva* L.) by *Agrobacterium turnerfaciens*. Plant Cell Physiol 33: 577–583

Charest P J, Hattori J, DeMoor J, Iyer V N, Miki B L (1990) In vitro study of transgenic tobacco expressing Arabidopsis wild type and mutant acetohydroxyacid synthase genes. Plant Cell Rpt 8:643–646

Christou P, Ford T L, Kofron M (1991) Production of transgenic rice (*Oryza saliva*) from agronomically important Indica and Japonica varieties via electric discharge particle acceleration of exogenous DNA into immature zygotic embryos. Bio/Tech 9: 957–962

Croughan T, (1996) Herbicide resistant rice. U.S. Pat. No. 5,545,822

Dietrich G E. (1998) Indazolinone resistant AHAS mutants. U.S. Pat. No. 5,731,180

Haughn G W, Smith J, Mazur B, Somerville C (1988) Transformation with a mutant Arabidopsis acetolactate synthase gene renders tobacco resistant to sulfonylurea herbicide. Mol Gen Genet 211: 266–271

Hayashimoto A, Li Z, Murai N (1990) A polyethylene glyco-mediated protoplast transformation system for production of fertile transgenic rice plants. Plant Physiol 93: 857–863

Hiei Y, Ohita S, Komari T, Kumashiro T (1994) Efficient transformation of rice (*Oriza saliva* L.) mediated by Agiobacterium and sequence analysis of the boundaries of the T-DNA. Plant J 6: 271–282

Ishida Y, Saito H, Ohta S, Hiei Y, Komari T, Kumashiro T. (1996). High efficiency transformation of maize (*Zea mays* L.) mediated by *Agrobactenium tumefaciens*. Nature Biotech 14:745–750

Lee L, Schroll R E, Grimes H D, Hodges T K (1989) Plant regeneration from indica rice (*Oryza saliva* L.) protoplasts. Planta 178: 325–333

Li L, Qu R, de Kochko A, Fauquet C, Beacy R N (1993) An improved rice transformation method using the biolistic method. Plant Cell Rep 12:250–255

Li Z, Hayashimot A, Murai N (1992) A sulfonylurea herbicide resistant gene from *Arabidopsis thaliaiia* as a new selectable marker for production of fertile transgenic rice plants. Plant Physiol 100: 662–668

Magha M l, Gurche P, Bregeon M, Renard M (1993) Characterization of a spontaneous rapeseed mutant tolerant to sulfonylurea and imidazolinone herbicides. Plant Breeding 111: 132–1141

Newhouse K, Singh B, Shaner D, Stidham M (1991) Mutations in corn (*Zea mays* L.) conferring resistance to imidazolinone herbicides. Theor Appl Genet 83: 65–70

Newhouse K E, Smith W, Starrett M A, Schaefer T J, Singh B (1992) Tolerance to imidazolinone herbicides in wheat. Plant Physiol 100: 882–886

Odell J T, Caimi P G, Yadav N S, Mauvais C J (1990) Comparison of increased expression of wild-type and herbicide-resistant acetolactate synthase genes in transgenic plants, and indication of posttranscriptional limitation on enzyme activity. Plant Physiol 94: 1647–1654

Ott K H, Kwagh J G, Stockton G W, Sidorov V, Kakefuda G (1996) Rational molecular design and genetic engineering of herbicide resistant crops by structure modeling and site-directed mutagenesis of acetohydroxyacid synthase. J Mol Biol 263: 359–368

Peng J, Lyznik L A, Lee L, Hodges T K (1990) Co-transformation of indica rice protoplasts with gusA and neo genes. Plant Cell Rept 9: 168–172

Peng J, Lyznik L A, Hodges T K (1991) Co-transformation of indica rice via PEG-mediated DNA uptake. Second International Rice Genetics Symposium pp 563–574

Peng J, Kononowicz H. Hodges T K (1992) Transgenic indica rice plants. Theor Appl Genet 83: 855–863

Peng J, Wen F, Lister R L, Hodges, T K (1995) Inheritance of gusA and neo genes in transgenic rice. Plant Molecular Biology 27: 91–104

Rathore K S, Chowdhury V K, Hodges T K (1993) Use of bar as a selectable marker gene for the production of herbicide-resistant rice plants from protoplasts. Plant Mol Biol 21: 871–884

Sathasivan K, Haughn G W, Mural N (1991) Molecular basis of imidazolinone herbicide resistance in *Arabidopsis thaliana* var Columbia. Plant Physiol 97: 1044–1050

Sebastian S A, Fader G M, Ulrich J F, Fomey D R, Chaleff R S (1989) Semidominant soybean mutation for resistance to sulfonylurea herbicides. Crop Sci 29:1403–1408

Shaner D L, Anderson P C, Stidham M A (1984) Imidazolinones. Potent inhibitors of acetohydroxyacid synthase. Plant Physiol 76: 545–546

Shaner D L, Robinson P A (1985) Absorption, translocation, and metabolism of AC 252,214 in soybean (*Glycin max*), common cocklebur (*Xanthium strumarium*), and velvetleaf (*Abutilon theophrasti*). Weed Sci 33: 469–471

Shimamoto K, Terada R, Izawa T, Fujimoto H (1989) Fertile transgenic rice plants regenerated from transformed protoplasts. Nature 338: 274–276

Singh B K, Stidham M A, Shaner D L (1988) Assay of acetohydroxyacid synthase. Anal Biochem 171: 173–179

Swanson E B, Herrgesell M J, Arnoldo M, Sippell D W, Wong R S C (1989) Microspore mutagenesis and selection: canola plants with field tolerance to the imidazolinones. Theor Appl Genet 78: 525–530

Tourneur C, Jouanin L, Vauzheret H (1993) Over expression of acetolactate synthase confers resistance to valine in transgenic tobacco. Plant Sci 88: 159–168

Wang H, Qi M, Cutler A J (1993) A simple method of preparing plant samples for PCR). Nucl Acids Res 21: 4153–4154

Westerfield, W W. (1 945) A calorimetric determination of blood acetoin. J. Biol. Chem. 161:495–502.

Patents Cited

Anderson P, Hibberd K A. 1984. Herbicide resistance in plants. U.S. Pat. No. 4,761,373

Bedbrook J R, Chaleff R S, Falco S C, Mazur B J, Somerville C R, Yadav N S. 1991. Nucleic acid fragment encoding herbicide resistant plant acetolactate synthase. U.S. Pat. No. 5,013,659

Croughan T, 1996. Herbicide resistant rice. U.S. Pat. No. 5,545,822

Dietrich G E. 1998. Imdazolinone resistant AHAS mutants. U.S. Pat. No. 5,731,180

Dietrich G E, 1998. Imidazolinone resistant AHAS mutants. U.S. Pat. No. 5,767,361

Dietrich G E, Smith J, Peng J. 1998. AHAS promoter useful for expression of introduced genes in plants. U.S. Pat. No. 5,750,866

Dietrich G E, Smith J, Peng J. 2000. Method of using as a selectable marker a nucleic acid containing AHAS promoter useful for expression of introduced genes in plants . U.S. Pat. No. 6,025,541

Hiei Y, Komari T. 1997. Method for transforming monocotyledons. U.S. Pat. No. 5,591,616

What is claimed is:

1. A method of using a maize mutant ahas 2 gene as a selectable marker, the method comprising the steps of:
   (a) transforming a rice protoplast with a nucleic acid construct comprising the maize mutant ahas 2 gene operably linked to a suitable promoter;
   (b) culturing the transformed rice protoplast of step (a) on a growth medium comprising an imidazolinone at a concentration of from 0.1 $\mu$M to 0.5 $\mu$M in an initial selection stage;
   (c) increasing the concentration of the imidazolinone during a second selection stage to a concentration of from 0.5 $\mu$M to 1 $\mu$M to select for one or more calli having increased resistance to the imidazolinone compared to a non-transformed rice protoplast;
   (d) inducing shoot and root formation from the one or more calli, optionally, in the absence of an imidazolinone; and
   (e) identifying transformed rice plant material produced from the one or more calli that grows in the presence of an imidazolinone.

2. The method according to claim 1, wherein the nucleic acid construct comprises at least one additional gene.

3. The method according to claim 2 further comprising measuring the transformation efficiency of the additional gene.

4. The method according to claim 1, wherein the maize mutant ahas 2 gene is a mutant X112 ahas gene.

5. The method according to claim 1, wherein the imidazolinone is an imidazolinone herbicide selected from the group consisting of imazethapyr, imazameth, imazapyr, imazamox, and imazaquin.

6. The method of claim 1, wherein the imidazolinone is imazethapyr or imazamox.

7. The method of claim 6, wherein the imidazolinone is imazethapyr.

8. A method of using a maize mutant ahas 2 gene as a selectable marker, the method comprising the steps of:
   (a) transforming a wheat embryo or a maize embryo with a nucleic acid construct comprising the maize mutant ahas 2 gene operably linked to a suitable promoter;
   (b) culturing the transformed wheat embryos or transformed maize embryos of step (a) on a growth medium comprising an imidazolinone at a concentration of from 0.05 $\mu$M to 0.1 $\mu$M in an initial selection stage to produce one or more calli;
   (c) increasing the concentration of the imidazolinone during a second selection stage compared to the concentration of the imidazolinone in the initial selection stage to select for one or more calli having increased resistance to the imidazolinone compared to a non-transformed calli;
   (d) inducing shoot formation by culturing the one or more calli in a growth medium comprising an imidazolinone;
   (e) inducing root formation from the one or more calli to produce regenerated plants, optionally, in the absence of an imidazolinone; and
   (f) spraying the regenerated plants with an imidazolinone in an amount effective to inhibit the growth of untransformed plants and allow transformed plants to grow.

9. The method of claim 8, wherein a wheat embryo is transformed.

10. The method of claim 8, wherein a maize embryo is transformed.

11. The method of claim 8, wherein the imidazolinone is imazethapyr or imazamox.

12. The method of claim 11, wherein the concentration of imazethapyr or imazamox during the second selection stage is from approximately 0.3 $\mu$M to 0.5 $\mu$M.

13. The method of claim 11, wherein the concentration of imazethapyr or imazamox during shoot induction is from approximately 0.1 $\mu$M to 0.25 $\mu$M.

14. The method of claim 11, wherein the concentration of imazethapyr or imazamox in the initial selection stage is from approximately 0.05 $\mu$M to 0.1 $\mu$M, the concentration of imazethapyr or imazamox during the second selection stage is from approximately 0.3 $\mu$M to 0.5 $\mu$M, and the concentration of imazethapyr or imazamox during shoot induction is from approximately 0.1 $\mu$M to 0.25 $\mu$M.

15. The method of claim 8, wherein a wheat embryo is transformed, the imidazolinone is imazamox, the concentration of imazamox in the initial selection stage is from approximately 0.05 $\mu$M to 0.1 $\mu$M, the concentration of imazamox during the second selection stage is from approximately 0.3 $\mu$M to 0.5 $\mu$M, and the concentration of imazamox during shoot induction is from approximately 0.1 $\mu$M to 0.25 $\mu$M.

16. The method of claim 8, wherein a wheat embryo is transformed, and wherein the imidazolinone is imazamox and the amount of imazamox in step (f) is from approximately 25 to 50 g/ha.

17. The method of claim 8, wherein a maize embryo is transformed, the imidazolinone is imazethapyr, the concentration of imazethapyr in the initial selection stage is from approximately 0.05 $\mu$M to 0.1 $\mu$M, the concentration of imazethapyr during the second selection stage is from approximately 0.3 $\mu$M to 0.5 $\mu$M, and the concentration of imazethapyr during shoot induction is from approximately 0.1 $\mu$M to 0.25 $\mu$M.

18. The method of claim 8, wherein a maize embryo is transformed, and wherein the imidazolinone is imazethapyr and the amount of imazethapyr in step (f) is from approximately 125 to 250 g/ha.

19. The method of claim 6, wherein the concentration of imazethapyr or imazemox in step (b) is 0.5 $\mu$M.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 1
agcagggagg cggtgcttgc                                                    20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 2
aagggtcaac attccagcgg t                                                  21
```